US010896742B2

(12) United States Patent
Girshick et al.

(10) Patent No.: US 10,896,742 B2
(45) Date of Patent: Jan. 19, 2021

(54) ESTIMATION OF PHENOTYPES USING DNA, PEDIGREE, AND HISTORICAL DATA

(71) Applicant: Ancestry.com DNA, LLC, Lehi, UT (US)

(72) Inventors: Ahna R. Girshick, Berkeley, CA (US); Natalie Telis, Mountain View, CA (US); Julie M. Granka, San Francisco, CA (US); Asher Keith Haug Baltzell, Salt Lake City, UT (US); Shiya Song, San Mateo, CA (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 16/669,530

(22) Filed: Oct. 31, 2019

(65) Prior Publication Data

US 2020/0135296 A1    Apr. 30, 2020

Related U.S. Application Data

(60) Provisional application No. 62/753,758, filed on Oct. 31, 2018.

(51) Int. Cl.
| | |
|---|---|
| *G16B 20/20* | (2019.01) |
| *G16B 40/20* | (2019.01) |
| *G16B 5/20* | (2019.01) |
| *G16B 20/40* | (2019.01) |
| *G16B 10/00* | (2019.01) |
| *G16B 40/30* | (2019.01) |

(52) U.S. Cl.
CPC .............. *G16B 20/20* (2019.02); *G16B 5/20* (2019.02); *G16B 10/00* (2019.02); *G16B 20/40* (2019.02); *G16B 40/20* (2019.02); *G16B 40/30* (2019.02)

(58) Field of Classification Search
CPC ........ G16B 20/20; G16B 10/00; G16B 40/30; G16B 5/20; G16B 20/40; G16B 40/20
USPC .......................................................... 702/20
See application file for complete search history.

(56) References Cited

U.S. PATENT DOCUMENTS

| | | | |
|---|---|---|---|
| 7,062,752 B2 | 6/2006 | Simpson et al. | |
| 7,076,504 B1 | 7/2006 | Handel et al. | |
| 7,630,986 B1 | 12/2009 | Herz et al. | |
| 7,783,665 B1 | 8/2010 | Tormasov et al. | |
| 7,818,396 B2 | 10/2010 | Dolin et al. | |
| 8,156,158 B2 | 4/2012 | Rolls et al. | |
| 8,187,811 B2 | 5/2012 | Eriksson et al. | |
| 8,510,057 B1 | 8/2013 | Avey et al. | |
| 8,589,437 B1 | 11/2013 | Khomenko et al. | |
| 8,744,982 B2 | 6/2014 | Crockett et al. | |
| 8,990,198 B2 | 3/2015 | Rolls et al. | |
| 9,092,391 B2 | 7/2015 | Stephan et al. | |
| 9,336,177 B2 | 5/2016 | Hawthorne et al. | |
| 9,367,663 B2 | 6/2016 | Deciu et al. | |
| 9,984,198 B2 | 5/2018 | Deciu et al. | |
| 10,437,858 B2 | 10/2019 | Naughton et al. | |
| 2002/0019746 A1 | 2/2002 | Rienhoff et al. | |
| 2002/0128860 A1 | 9/2002 | Leveque et al. | |
| 2002/0138572 A1 | 9/2002 | Delany et al. | |
| 2003/0129630 A1 | 7/2003 | Aakalu et al. | |
| 2004/0093334 A1 | 5/2004 | Scherer | |
| 2005/0027560 A1 | 2/2005 | Cook | |
| 2005/0152905 A1 | 7/2005 | Omoigui | |
| 2005/0164704 A1 | 7/2005 | Winsor | |
| 2007/0027917 A1 | 2/2007 | Ariel et al. | |
| 2007/0061085 A1 | 3/2007 | Fernandez | |
| 2007/0226250 A1 | 9/2007 | Mueller et al. | |
| 2008/0021288 A1 | 1/2008 | Bowman et al. | |
| 2008/0033899 A1 | 2/2008 | Barnhill et al. | |
| 2008/0082955 A1 | 4/2008 | Andreessen et al. | |
| 2008/0091471 A1 | 4/2008 | Michon et al. | |
| 2008/0097938 A1 | 4/2008 | Guyon et al. | |
| 2008/0131887 A1 | 6/2008 | Stephan et al. | |
| 2008/0162510 A1 | 7/2008 | Baio et al. | |
| 2008/0201174 A1 | 8/2008 | Ramasubramanian et al. | |
| 2008/0228797 A1 | 9/2008 | Kenedy et al. | |

(Continued)

FOREIGN PATENT DOCUMENTS

| | | |
|---|---|---|
| WO | WO-2008/067551 | 6/2008 |
| WO | WO-2010/139006 | 12/2010 |

(Continued)

OTHER PUBLICATIONS

PCT International Search Report and Written Opinion, PCT Patent Application No. PCT/IB2019/059366, dated Feb. 7, 2020, 12 pages.
Do, C.B. et al., "Comparison of Family History and SNPs for Predicting Risk of Complex Disease," PLOS Genetics, Oct. 2012, vol. 8, No. 10, pp. 1-16.
Gim, J. et al., "Improving disease prediction by incorporating family disease history in risk prediction models with large-scale genetic data," Genetics: Early Online, Sep. 12, 2017, 18 pages.
Jiang, J. et al., "Joint prediction of multiple quantitative traits using a Bayesian multivariate antedependence model," Heredity, Jan. 23, 2015, vol. 115, pp. 29-36.

(Continued)

*Primary Examiner* — Jerry Lin
(74) *Attorney, Agent, or Firm* — Fenwick & West LLP

(57) ABSTRACT

Disclosed are techniques for predicting a trait of an individual and identifying a set of enriched record collections of a genetic community. To predict a trait of an individual, DNA features and non-DNA features of the individual are accessed to generate a feature vector that is inputted into a machine learning model. The machine learning model generates a prediction of the trait. The prediction may be based on an inheritance prediction and/or a community prediction. To identify a set of enriched record collections, individuals belonging to a genetic community are identified and a set of candidate record collections are accessed. A community count and a background count is determined for each candidate record collection. The set of enriched record collections are identified based on a comparison of the community count and the background count. The genetic community may be annotated using the set of enriched record collections.

26 Claims, 14 Drawing Sheets

(56) References Cited

U.S. PATENT DOCUMENTS

| | | |
|---|---|---|
| 2009/0043752 A1 | 2/2009 | Kenedy et al. |
| 2009/0077110 A1 | 3/2009 | Petri |
| 2009/0099789 A1 | 4/2009 | Stephan et al. |
| 2009/0112871 A1 | 4/2009 | Hawthorne et al. |
| 2009/0132284 A1 | 5/2009 | Fey et al. |
| 2009/0299645 A1 | 12/2009 | Colby et al. |
| 2010/0042438 A1 | 2/2010 | Moore et al. |
| 2010/0070455 A1 | 3/2010 | Halperin et al. |
| 2011/0098193 A1 | 4/2011 | Kingsmore et al. |
| 2013/0129630 A1 | 5/2013 | Haik |
| 2013/0204901 A1 | 8/2013 | Pottathil |
| 2013/0230858 A1 | 9/2013 | Cantor et al. |
| 2013/0345988 A1 | 12/2013 | Avey et al. |
| 2016/0186266 A1 | 6/2016 | Alarcon |
| 2016/0277408 A1 | 9/2016 | Hawthorne et al. |
| 2016/0350479 A1 | 12/2016 | Han et al. |
| 2017/0009788 A1 | 1/2017 | Sawchuk |
| 2017/0277828 A1 | 9/2017 | Avey et al. |
| 2017/0293861 A1 | 10/2017 | Roy et al. |
| 2017/0329924 A1 | 11/2017 | Macpherson et al. |

FOREIGN PATENT DOCUMENTS

| | | |
|---|---|---|
| WO | WO-2015/173435 | 11/2015 |
| WO | WO-2017/009788 | 1/2017 |

OTHER PUBLICATIONS

Lyssenko, M.D., et al., "Clinical Risk Factors, DNA Variants, and the Development of Type 2 Diabetes" The New England Journal of Medicine, vol. 359, Nov. 20, 2008, pp. 2220-2232. <doi:10.1056/NEJMoa0801869>.

Mealiffe, M.E. et al., "Assessment of Clinical Validity of a Breast Cancer Risk Model Combining Genetic and Clinical Information" J. Natl. Cancer Institute (JNCI), vol. 102, No. 21, Nov. 3, 2010, pp. 1618-1627.

Morrison, A C., et al. "Prediction of Coronary Heart Disease Risk using a Genetic Risk Score: The Atherosclerosis Risk in Communities Study," American Journal of Epidemiology, vol. 166, No. 1, Apr. 18, 2007, pp. 28-35.

Pedregosa, et al., "5.3 Preprocessing data," Scikit-learn: Machine Learning in Python, JMLR 12, pp. 2825-2830, 2011, [Online] [Retrieved Nov. 6, 2019], Retrieved from the internet <URL: https://scikit-learn.org/stable/modules/preprocessing.html#encoding-categorical-features.

Polubriaginof, F. et al., "Estimate of disease heritability using 7.4 million familial relationships inferred from electronic health records," bioRxiv, Cold Spring Harbor Laboratory, Jul. 28, 2016, 27 pages.

Preliminary Amendment dated Aug. 4, 2017 filed in U.S. Appl. No. 15/621,985, 6 pages.

Ruderfe, D.M. et al., "Family-based genetic risk prediction of multifactorial disease" Genome Medicine, vol. 2:1, Jan. 15, 2010, pp. 1-7.

Schabath, M.B., et al. "Cancer Epidemiology, Biomarkers & Prevention: Combined Effects of the p53 and p73 Polymorphisms on Lung Cancer Risk," Cancer Epidemiol Biomarkers Prev., Jan. 24, 2006, vol. 15, pp. 158-161.

Scheuner, et al., "Family History: A Comprehensive Genetic Risk Assessment Method for the Chronic Conditions of Adulthood" American Journal of Medical Genetics, Wiley-Liss, Inc., vol. 71, 1997, pp. 315-324.

Tung et al. 2011, PLoSOne vol. 6 No. 8 e23473.

Yoon, P.W. et al., "Developing Family Healthware, a Family History Screening Tool to Prevent Common Chronic Diseases" Preventing Chronic Disease: Public Health Research, Practice, and Policy, vol. 6, No. 1, Jan. 2009, pp. 1-11.

900

```
┌─────────────────────────────────────────────────┐
│ Identify individuals belonging to a genetic community │
│                       905                       │
└─────────────────────────────────────────────────┘
                         │
                         ▼
┌─────────────────────────────────────────────────┐
│     Access a set of candidate record collections │
│                       910                       │
└─────────────────────────────────────────────────┘
                         │
                         ▼
┌─────────────────────────────────────────────────┐
│ Determine a community count for each candidate record │
│                 collection in the set            │
│                       915                       │
└─────────────────────────────────────────────────┘
                         │
                         ▼
┌─────────────────────────────────────────────────┐
│ Determine a background count of each candidate record │
│                 collection in the set            │
│                       920                       │
└─────────────────────────────────────────────────┘
                         │
                         ▼
┌─────────────────────────────────────────────────┐
│      Identify a set of enriched record collections │
│                       925                       │
└─────────────────────────────────────────────────┘
```

```
┌─────────────────────────────────────────────────┐
│ Determine a community frequency for one or more │
│ characteristics associated with individuals in  │
│              the genetic community              │
│                      1005                       │
└─────────────────────────────────────────────────┘
                         │
                         ▼
┌─────────────────────────────────────────────────┐
│  Determine a background frequency for each of   │
│              the characteristics                │
│                      1010                       │
└─────────────────────────────────────────────────┘
                         │
                         ▼
┌─────────────────────────────────────────────────┐
│ Identify an enriched characteristic among the   │
│ individuals in the genetic community based on   │
│   the community frequency and the background    │
│                    frequency                    │
│                      1015                       │
└─────────────────────────────────────────────────┘
```

ESTIMATION OF PHENOTYPES USING DNA, PEDIGREE, AND HISTORICAL DATA

CROSS-REFERENCE TO RELATED APPLICATION

The present application claims the benefit of U.S. Provisional Patent Application No. 62/753,758 filed on Oct. 31, 2018, which is hereby incorporated by reference in its entirety.

TECHNICAL FIELD

The disclosed embodiments relate to assessing populations in which variants of interest may have arisen and propagated and discovering historical populations from the pattern of genetic relationships between people.

BACKGROUND

Although humans are, genetically speaking, almost entirely identical, small differences in human DNA are responsible for some observed variations between individuals. The human genome mutation rate is estimated to be $1.1*10^{-8}$ per site per generation. This leads to a variant approximately every 300 base pairs. Most of the mutations that are passed down to descendants are related to single-nucleotide polymorphism (SNP). SNP is a substitution of a single nucleotide that occurs at a specific position in the genome. Learning about population structure from genetic polymorphism data is an important topic in genetics.

Further, links between genomic data and genealogical data are currently unknown, but could provide insight into the characterizations of different genetic communities. In addition, current methods of characterizing and creating content for genetic communities, require record collections to be manually analyzed. This is a time-consuming process and does not take advantage of all relevant record collections.

SUMMARY

Disclosed herein relates to example embodiments for predicting a trait of a target individual. In one embodiment, a method for predicting a trait of a target individual includes accessing DNA features and non-DNA features of the target individual. A feature vector is generated that combines the DNA features and non-DNA features of the target individual and includes a set of numerical values representing the features. The features that are added to the feature vector may be DNA features and/or non-DNA features are that disproportionately associated with individuals in different genetic communities. The feature vector is inputted into a machine learning model to generate a prediction of whether the target individual has the trait. In some embodiments, the prediction is based on an inheritance probability, which represents the likelihood the target individual inherited the trait from one or more relatives. In some embodiments, the prediction is also based on a community probability, which represents the likelihood the target individual has the trait based on a prevalence of the trait among a genetic community of the target individual. In some embodiments, the machine learning model is trained using the DNA and non-DNA features of sample individuals, who are individuals that affirmatively have or affirmatively do not have the trait.

In another embodiment, the techniques disclosed herein may be used to predict a set of enriched record collections for a genetic community. In one embodiment, a method of predicting the set of enriched record collections of a genetic community includes identifying individuals belonging to the genetic community and accessing a set of candidate record collections. A community count and background count is determined for each candidate record collection. A community count represents how often a candidate record collection is associated with individuals in a genetic community, and a background count represents how often a candidate record collection is associated with individuals in one or more genetic communities. Enriched record collections are identified by comparing the community counts and background counts of the candidate record collections. Enriched record collections can be used to estimate the aggregate traits and historical environments of a genetic community at different points in history. For example, enriched record collections may be used to annotate genetic communities with historical, social, and/or economic details. These annotations may guide users exploring the characteristics of a genetic community. Enriched record collections may also be used to generate additional content for genetic communities using natural language processing techniques and computer vision techniques.

In another embodiment, the techniques disclosed herein may be used to identify enriched characteristics among individuals belonging to a genetic community. In one embodiment, methods of identifying enriched characteristics include identifying one or more characteristics of a genetic community using the set of enriched record collections of the genetic community. A community frequency and a background frequency is determined for each characteristic. A community frequency is based on how often a characteristic is associated with the individuals belonging to the genetic community, and a background frequency is based on how often a characteristic is exhibited in individuals among a plurality of genetic communities. Enriched characteristics of the genetic community are identified based on a comparison of the community frequencies and background frequencies of the one or more characteristics. The enriched characteristics of different genetic communities may be compared to determine which characteristics are unique to each genetic community. Similarly, enriched characteristics among different subsets of a genetic communities may be identified and compared to generate an aggregate spatial-temporal description of the genetic community. An aggregate spatial-temporal description provides insight into the changes in the phenotypes and/or historical environments of a genetic community over time and space.

In yet another embodiment, a non-transitory computer readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

BRIEF DESCRIPTION OF THE DRAWINGS

FIG. 9 illustrates a method of predicting a set of enriched records collections for a genetic community, in accordance with an embodiment.

FIG. 10 illustrates a method of identifying an enriched characteristic of a genetic community, in accordance with an embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Example System Environment

Figure 1:
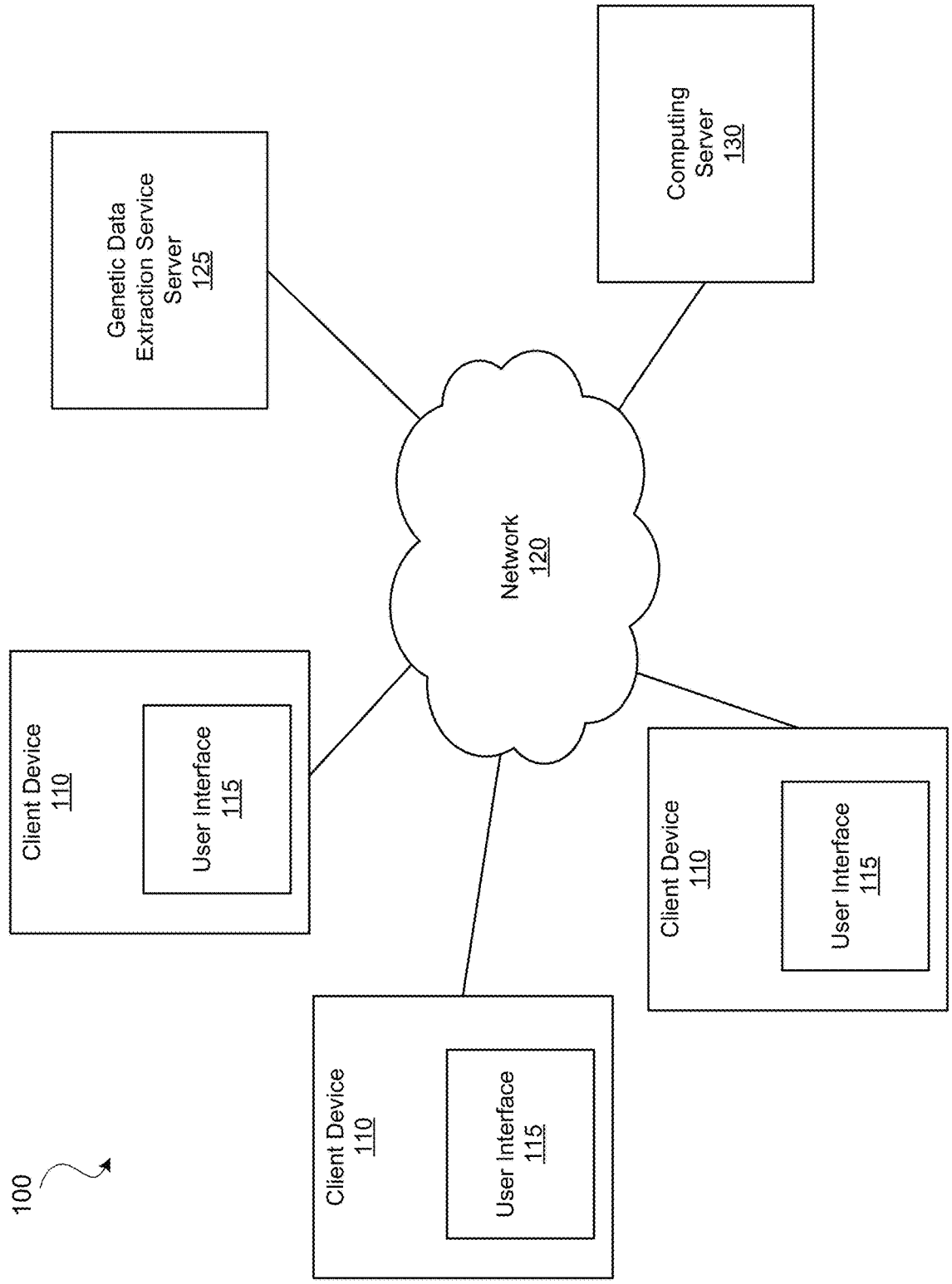
FIG. 1 illustrates a diagram of a system environment of an example computing system, in accordance with an embodiment.

FIG. 1 illustrates a diagram of a system environment 100 of an example computing server 130, in accordance with an embodiment. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliance (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In one embodiment, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the client device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In one embodiment, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. In one embodiment, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms. For example, in one embodiment, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. In one embodiment, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual.

The computing server 130 performs various analysis of the genetic data, genealogical data, and users' survey responses to generate results regarding the phenotypes and genealogy of users of computing server 130. Depending on the embodiments, the computing server 130 may also be referring to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnic compositions of users, paternal and maternal genetic analysis, potential family relatives, ancestor information, analyses of DNA data, potential or identified phenotypes of users (e.g., diseases, traits, and other characteristics), etc. The computing server 130 may present or cause the user interface 115 to present the results to the users through a GUI displayed at the client device 110. The results may include graphical elements, textual information, data, charts, and other elements such as family trees.

In one embodiment, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In one embodiment, subject to the user's privacy settings and authorization, the computing server 130 may allow the user's genetic dataset to be linked to the user profile and to one or more of the family trees. The users may also authorize the computing server 130 to analyze their genetic dataset and allow their profiles to be discovered by other users.

Example Computing Server Architecture

Figure 2:
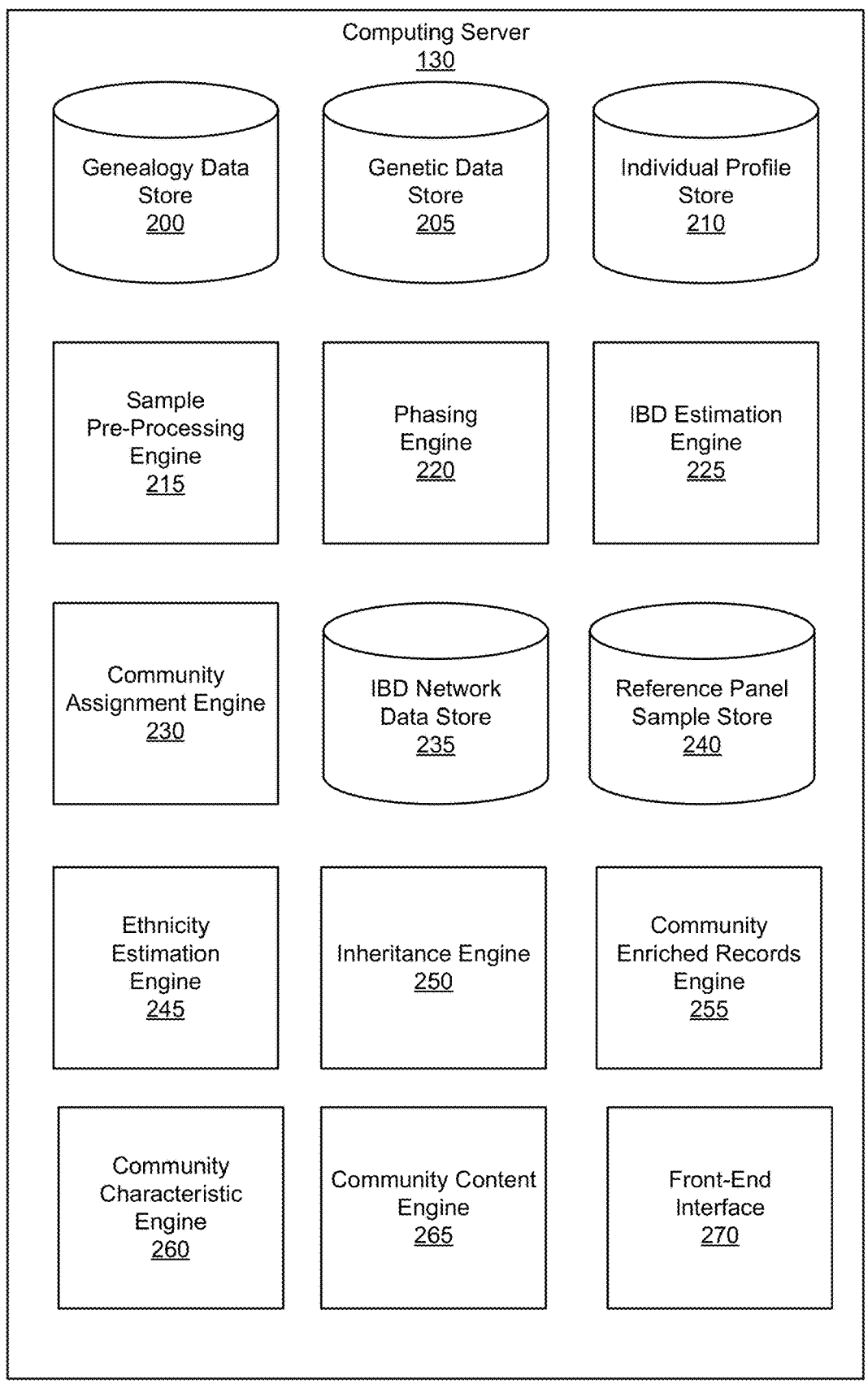
FIG. 2 is a block diagram of an architecture of an example computing system, in accordance with an embodiment.

FIG. 2 is a block diagram of an architecture of an example computing server 130, in accordance with an embodiment. In the embodiment shown in FIG. 2, the computing server 130 includes a genealogy data store 200, a genetic data store 205, an individual profile store 210, a sample pre-processing engine 215, a phasing engine 220, an IBD estimation engine 225, a community assignment engine 230, an IBD network data store 235, a reference panel sample store 240, an ethnicity estimation engine 245, an inheritance engine 250, a community records engine 255, a community attributes engine 260, a community content engine 265, and a front-end interface 270. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogical data, and survey response data. The computing server 130 processes the genetic data of users to identify shared identity-by-descent (IBD) segments between individuals. The genealogical data and survey response data may be part of user profile data. The amount and type of user profile data stored for each user may vary based on the information of a user, which is provided by the user as she creates an account and profile at a system operated by the computing server 130 and continues to build her profile, family tree, and social network at the system, and as she continues to link her profile with her genetic data. Users may provide data via the user interface 115 of a client device 110. Initially, and as a user continues to build her genealogical profile, the user may be prompted to answer simple questions related to basic demographic information (e.g., name, date of birth, birthplace, etc.). Later on, a user may be prompted to answer more advanced questions that may be useful for obtaining additional genealogical and survey data, including survey questions regarding various traits, characteristics, preferences, habits, lifestyle, environment, etc. of the users.

Genealogical data may be stored in the genealogy data store 200 and may include various types of data that are related to tracing family relatives of users. Examples of genealogical data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of that individual (e.g., the recorded relationships in the family). The family tree information associated with a user includes one or more specified nodes. Each node in the family tree represents the individual, an ancestor of the individual who might have passed down genetic material to the individual, and the individual's other relatives including siblings, cousins, offspring in some cases. Genealogical data may also include connections and relationships among users of the computing server 130. The information related to the connections among a user and her relatives that may be associated with a family tree may also be referred to as pedigree data or family tree data.

In addition to user-input data, genealogical data may also take other forms that are obtained from various sources such as public records and third-party data collectors. For example, genealogical records from public sources include birth records, marriage records, death records, census records, court records, probate records, adoption records, obituary records, etc. Likewise, genealogical data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a medical record database, a local history records database, a business registration database, a motor vehicle database, and the like.

Furthermore, the genealogy data store 200 may also include relationship information inferred from the genetic samples stored in the genetic data store 205 and information received from the individuals. For example, the relationship information may include which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data and corresponding metadata. A genetic dataset may contain data of the whole or portions of an individual's genome. The genetic data store 205 may store a pointer to a location associated with the genealogy data store 200 associated with the individual. A genetic dataset may take different forms. In one embodiment, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP sites (e.g., allele sites) filtered from the sequencing results. A SNP site may be associated with a unique identifier. The genetic dataset may be in a form of a diploid dataset that includes a sequencing of genotypes, such as genotypes at the target SNP sites, or the whole base pair sequence that includes genotypes at known SNP sites that vary between individuals and other base pair sites that are not commonly associated with known SNP sites. The diploid dataset may be referred to as a genotype dataset or a genotype sequence. Genotypes may have different meanings in various contexts. In one context, an individual's genotype may refer to a collection of diploid alleles of an individual. In other contexts, a genotype may be a pair of alleles present on two chromosomes of an individual at a given genetic marker, such as a SNP site.

A genotype at a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store which nucleotide corresponds to the first allele and which nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences.

The individual profile store 210 stores profiles and related metadata associated with various individuals appearing in the computing server 130. A computing server 130 may use unique individual identifiers to identify various users and other non-users that might appear in other data sources, such as ancestors or historical persons who appear in any family tree or genealogical database. A unique individual identifier may include a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointers associating genetic datasets such as genotype and phased haplotype data of the individual that are saved in the genetic data store 205. The metadata about the individual may also include individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, preferences, location, and the like. In one embodiment, the user profile data may also include one or more photos of the users and photos of relatives (e.g., ancestors) of the users that are uploaded by the users.

User profile data may also be obtained from other suitable sources, including historical records (e.g., records related to an ancestor), medical records, military records, photographs, other records indicating one or more traits, and other suitable recorded data. For example, the computing server 130 may present various survey questions to its users from time to time. The responses to the survey questions may be stored in the profiles maintained by the individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have family history as one of the risk factors, questions regarding any diagnosis of increased risk of any diseases or disorders, and questions concerning wellness-related issues such as family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's diseases, diabetes, cancer, and obesity. The computing server 130 may obtain data of a user's disease-related phenotypes from survey questions of health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as ability to sense an asparagus metabolite. Traits may also be collected from historical records, electronic health records, and electronic medical records.

The computing server 130 also may present various survey questions related to environmental factors of users. In this context, an environmental factor may be a factor that is not directly connected to the genetics of the users. The environmental factors may also be referred to as the traits of the users. Environmental factors may include users' preferences, habits, and lifestyle. For example, a survey regarding users' preferences may include questions related to things and activities that users like or dislike, such as types of music a user enjoys, sports a user plays, social preferences, video games preferences, etc. Other questions may be related to the users' diet preferences, such as the like or dislike of certain types of food (e.g., dairy, eggs). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g. stretching, flexibility, heart rate recovery), family type (adopted family or not, has siblings or not, lived with extended family during childhood), property and item ownership (has home or rents, has smartphone or doesn't, has car or doesn't).

Surveys also may be related to other environmental factors such as geographical, socioeconomic, or cultural factors. Geographical questions may include questions related to the birth location, family migration history, town or city of users' current or past residence. Socioeconomic questions may be related to users' education level, income, occupations, self-identified demographic groups, etc. Questions related to culture may concern users' religions, native language, language spoken at home, customs, dietary practices, etc. Other questions related to users' cultural and behavioral questions are also possible. Questions may also ask about users' beliefs or opinions, such as political opinions, religious beliefs, opinions on certain debates, events, and controversies, and opinions/beliefs on any suitable things or concepts. The beliefs and opinions may also be regarded as the traits of the users.

For any survey question asked, the computing server 130 may also ask an individual the same or similar questions regarding the traits of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogical data store 200 and genetic data store 205.

The user profile data, survey response data, the genetic data, and the genealogical data may be subject to privacy and authorization settings from the users. For example, when presented with a survey question, a user may select to answer or skip the question. The computing server 130 may present users from time to time with information regarding users' selection of the extent of information and data shared. The computing server 130 also may maintain and enforce one or more privacy settings for users in connection with the access of the user profile data, genetic data, and other sensitive data. For example, the user may pre-authorize access of the data and may change the setting as wished. The privacy settings also may allow a user to specify (e.g., by opting out, by not opting in) whether the computing server 130 may receive, collect, log, or store particular data associated with the user for any purpose. A user may restrict her data at various levels. For example, in one level, the data may not be accessed by the computing server 130 for purposes other than displaying the data in the user's own profile. On another level, the user may authorize anonymization of her data and participate in studies and research conducted by the computing server 130 such as a large scale genetic study. In yet another level, the user may turn some portions of her genealogical data public to allow the user to be discovered by other users (e.g., potential relatives) and be connected in one or more family trees. Access or sharing of any information or data in the computing server 130 may also be subject to one or more similar privacy policies.

The sample pre-processing engine 215 receives and pre-processes data received from various sources to change the data into a format used by the computing server 130. For genealogical data, the sample pre-processing engine 215 may receive data from an individual via the user interface 115 of the client device 110. To collect user data (e.g., genealogical and survey data), the computing server 130 may cause an interactive user interface 115 on the client device 110 to display interface elements in which users can provide genealogical data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from the genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. The human genome mutation rate is estimated to be $1.1*10^{-8}$ per site per generation. This leads to a variant approximately every 300 base pairs. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. For example, 700,000 autosomal SNPs may be identified in an individual's data and may be stored in genetic data store 205. Alternatively, in one embodiment, a genetic dataset may include at least 10,000 SNP sites. In another embodiment, a genetic dataset may include at least 100,000 SNP sites. In yet another embodiment, a genetic dataset may include at least 500,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic datasets into pairs of haploid genetic datasets. An individual's haplotype may refer to a collection of alleles (e.g., a sequence of alleles) that are inherited from a parent. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP site of a pair of chromosomes but may not be able to distinguish which allele belongs to which specific chromosome. The phasing engine 220 uses a genotype phasing algorithm to assign one allele to a first chromosome and another allele to a second chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as training sample because the correct phasing of the child is almost certain by comparing the child's genotypes to the parent's genetic datasets. The haplotype-cluster model may be generated iteratively along with the phasing process with a large number of unphased genotype datasets.

By way of example, the phasing engine 220 may use a directed acyclic graph model such as a hidden Markov model (HMM) to perform phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes, may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. patent application Ser. No. 15/591,099, entitled "Haplotype Phasing Models," filed on Oct. 19, 2015, describes one possible embodiment of haplotype phasing.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicate the mismatch is not attributable to potential errors in phasing. The IBD estimation engine 225 determines the total length of matched segments, which may also be referred to as IBD segments. The length may be measured in the genetic distance in the unit of centimorgans (cM). The computing server 130 may save data regarding individual pairs who share a length of IBD segments exceeding a predetermined threshold (e.g., 6 cM), such as in the genealogy data store 200. U.S. patent application Ser. No. 14/029,765, entitled "Identifying Ancestral Relationships Using a Continuous stream of Input," filed on Sep. 17, 2013, and U.S. patent application Ser. No. 15/519,104, entitled "Reducing Error in Predicted Genetic Relationships," filed on Apr. 13, 2017, describe example embodiments of IBD estimation.

Typically, individuals who are closely related share a relatively large number of IBD segments, and the IBD segments tend to have greater lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments between two individuals.

Community assignment engine 230 assigns individuals to one or more genetic communities. A genetic community may correspond to an ethnic origin or a group of people descended from a common ancestor. The granularity of genetic community classification may vary depending on embodiments and methods used in assigning communities. For example, in one embodiment, the communities may be African, Asian, European, etc. In another embodiment, the European community may be divided into Irish, German, Swedish, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region. A genetic community may also refer to an ethnic group, a DNA circle (e.g., individuals connected via an IBD network), a family, and the like.

The community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. patent application Ser. No. 15/168,011, entitled "Discovering Population Structure from Patterns of Identity-By-Descent," filed on May 28, 2016, describes one possible embodiment of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. Some individuals' genetic data may be the most representative of a genetic community. Their genetic datasets may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belong to a community, in determining the ethnic composition of an individual, and in determining the accuracy in any genetic data analysis, such as by computing a posterior probability of a classification result from a classifier.

A reference panel sample may be identified in different ways. In one embodiment, an unsupervised approach in community detection may apply the clustering algorithm recursively for each identified cluster until the sub-clusters contain a number of nodes that is smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected.

The ethnicity estimation engine 245 estimates the ethnicity composition of a genetic dataset of a target individual. The genetic datasets used may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In one embodiment, the ethnicity estimation engine 245 divides a target genetic dataset into a plurality of windows (e.g., about 1000 windows). Each window includes a small number of SNP sites (e.g., 300 SNP sites). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of levels. Each level, representing a window, include a plurality of nodes. The nodes representing different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNP sites belongs to a second ethnicity. Each level includes multiple nodes so that there are many possible paths to traverses the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNP sites in the window. The ethnicity estimation engine 245 determines the emission probabilities by comparing SNP sites in the window corresponding to the target genetic dataset to corresponding SNP sites in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. patent application Ser. No. 15/209,458, entitled "Local Genetic Ethnicity Determination System," filed on Jul. 13, 2016, describes an example embodiment of ethnicity estimation.

The inheritance engine 250 predicts a trait of an individual based on the DNA and non-DNA data of a target individual and data of individuals genetically related to the target individual using one or more machine learning models. DNA data may include data of the whole or portions of the individual's genome. Examples of DNA data may include genetic data, such as sequences of genetic markers, such as target SNP sites; diploid data that include sequencing genotypes, such as genotypes at the target SNP sites or the whole base pair sequence that includes genotypes at known SNP sites; haploid data from phased diploid data; and the like. Non-DNA data may include full or partial pedigree structure, birth years, genders, historical records such as data of users' ancestors, medical records such as electronic health records, electronic medical records and family health histories, survey responses, census records, military service records, immigration records, birth, death or marriage certificates, photographs of individuals and their relatives and ancestors, and the like. Non-DNA data may also include ethnicity, relationship to family members, carrier status, and the like. Additional data may also be used to predict a trait of an individual, such as the prevalence of a trait among members of different genetic communities. The inheritance engine 250 generates a prediction of the trait by inputting the DNA and non-DNA data as a feature vector into a machine learning model. The machine learning model may be trait and/or genetic community specific. In some embodiments, the inheritance engine 250 propagates trait predictions to members of the individual's family tree to predict the trait of living and historical relatives of the individual.

The community enriched records engine 255 identifies enriched record collections of different genetic communities. In some embodiments, the community records engine 255 identifies enriched record collections based on the frequency with which different record collections are associated with members of a genetic community. Alternatively, or additionally, the community records engine 225 may identify enriched record collections based on a normalized distribution of record collections throughout different genetic communities identified by the computing server 130. The community enriched records engine 255 may provide enriched record collections to members of a genetic community on a user interface 115. Enriched record collections can be used to estimate the aggregate traits and historical environments of a genetic community at different points in history. For example, enriched record collections may be used to annotate genetic communities with historical, social, and/or economic details. These annotations may guide users of the computing server 130 exploring the characteristics of a genetic community. Additionally, enriched record collections can be used to characterize previously uncharacterized and/or unidentified genetic communities.

The community characteristic engine 260 identifies which characteristics are enriched in different genetic communities. In one embodiment, the community characteristic engine 260 compares how frequently a characteristic is associated with a genetic community and how frequently the characteristic is associated with all or some of the genetic communities identified by the computing server 130. In other embodiments, the community characteristic engine 260 identifies enriched characteristics by identifying the odds that a member of the genetic community has a characteristic over the odds that a member of the genetic community does not have the characteristic (e.g., an odds ratio). The community characteristic engine 260 may identify enriched characteristics using the enriched record collections of a genetic community, and data stored in the genealogy data store 200, genetic data store 205, and individual profile store 210. In some embodiments, the community characteristic engine 260 identifies enriched characteristics for subsets of genetic communities to generate a spatial-temporal description of a genetic community. The community attributes engine 260 may also compare which characteristics (e.g., traits and/or environmental conditions) are enriched among different genetic communities and/or different subsets of the same genetic community. By comparing enriched characteristics of different genetic communities, the community characteristic engine 260 may determine which communities are more likely to have a particular phenotype or environmental history. For example, the community characteristic engine 260 may identify which occupations were prevalent among members of a first genetic community and scarce among members of a second genetic community. Alternatively, or additionally, the community characteristic engine 260 may identify which occupations were enriched among different time periods within the same genetic community by generating aggregate spatial-temporal descriptions of the genetic community.

The community content engine 265 creates content for a genetic community based on the enriched record collections identified by the community enriched records engine 255 and/or the community enriched characteristics identified by the community characteristic engine 260. Data may be automatically extracted from records using natural language processing techniques, such optical character recognition. The community content engine 265 may summarize extracted data across records to generate content for a genetic community. Content created by the community content engine 265 may be stored by the computing server 130 and accessed by users through the front-end interface 270.

The front-end interface 270 may display various results determined by the computing server 130. The results and data may include the IBD affinity between a user and another individual, the community assignment of the user, the ethnicity estimation of the user, phenotype prediction and evaluation, genealogical data search, family tree and pedigree, relative profile and other information. The front-end interface 270 may be a graphical user interface (GUI) that displays various information and graphical elements. The front-end interface 270 may take different forms. In one case, the front-end interface 270 may be a software application that can be displayed at an electronic device such as a computer or a smartphone. The software application may be developed by the entity controlling the computing server 130 and be downloaded and installed at the client device 110. In another case, the front-end interface 270 may take the form of a webpage interface of the computing server 130 that allows users to access their family tree and genetic analysis results through web browsers. In yet another case, the front-end interface 270 may provide an application program interface (API).

Example Trait Prediction Machine Learning Models

Figure 3:
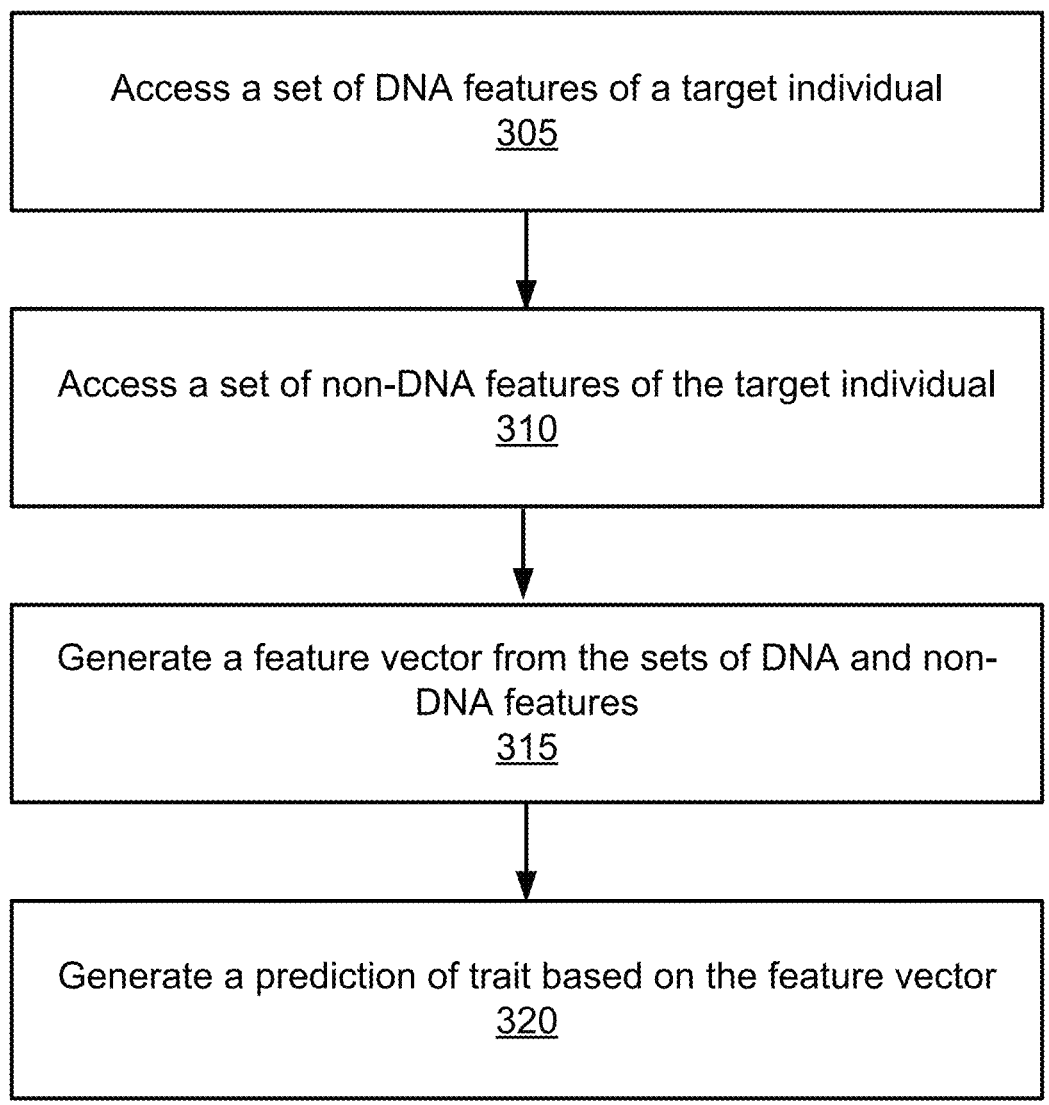
FIG. 3 illustrates a method of predicting a trait of a target individual, in accordance with an embodiment.

FIG. 3 illustrates a method 300 of predicting a trait of a target individual, in accordance with an embodiment. To predict a trait of the target individual, a set of DNA features of a target individual are accessed 305. DNA features are derived from DNA data, which may include sequences of genetic markers, such as target SNP sites; diploid data that include sequencing genotypes, such as genotypes at the target SNP sites or the whole base pair sequence that includes genotypes at known SNP sites; haploid data from phased diploid data; and the like.

A set of non-DNA features derived from non-DNA data of the target individual is also accessed 310 from data stored in the genealogy data store 200. Non-DNA features may include information extracted from a family tree of the target individual. In some embodiments, information stored in family trees is digitally encoded. Examples of information stored in the trees may include full or partial pedigree structure, birth years, genders, marital/genetic connections between individuals in the family tree, and the like. Non-DNA features may also include historical record data and medical record data from the historical and medical records of the target individual and relatives of the target individual. Historical records and medical records may include digital photographs, census data, court records, adoption records, marriage records, probate records, and other recorded data including videos and audio recordings. Survey responses of the target individual and living relatives of the target individual who are users of the computing server 130 may also be accessed. Survey responses may be obtained from surveys provided to users on the front-end user interface 270 and stored in the individual profile store 210. Further, non-DNA features may include other data such as ethnicity compositions, relationships to family members, carrier status, age, sex, polygenic risk scores, information about a sequencing array, location of purchase, location of residence, residence type, other socioeconomic information, lifestyle, health, covariates, and the like.

In some embodiments, to extract DNA features and non-DNA features from record data, records associated with the target individual and the genetic community of the target individual are filtered using different quality controls. Quality controls may include filtering out data with gender and/or age mismatches. Quality controls may also include data consolidation. For example, historical and medical data may be filtered by consolidating spelling variants across regions and time periods to include only a portion of spelling variants. Data may also be filtered based on a frequency or prevalence of a datum among the records of individuals in a genetic community. For example, a job title may only be analyzed if it is associated with a threshold number of individuals.

A feature vector is generated 315 for the target individual from the sets of DNA and non-DNA features using one or more numerical encoding techniques. Feature vectors may be represented as a set of numerical values that each represent a DNA or non-DNA feature of the target individual and relatives of the target individual. In some embodiments, to generate 315 a feature vector, the non-DNA features may be normalized so that the non-DNA features have a common format and can be aggregated across records. Normalization may be used when features have colloquial names that are community or period specific, such as the names of occupations or medical conditions. An example of data normalization may include the consolidation of spelling variants of job titles based on abbreviations, historical names, regional names, and the like. To generate 315 a feature vector, the features may also be coded. The non-DNA features may be coded as counts of the number of members of the target individual's family tree that have a feature. Counts may be family-tree wide, or be generational or branch specific (e.g., material counts, paternal counts, generational counts, etc.). DNA features may also be coded. For example, SNP features may be coded numerically so that features related to homozygous minor, heterozygous, and homozygous major alleles may be distinguishable in the feature vector.

Certain machine learning algorithms may be quite sensitive to processing features with different distributions. For example, combining DNA features (SNP values 0, 1, 2) with non-DNA features (e.g., historical zip code, ahnentafel number, historical eye color name, historical occupation, historical birth years, etc.) may generate a better performance if these features are normalized to a distribution with a predetermined range (e.g., a unit norm distribution). In some embodiments, the features in feature vector may not need to be normalized to the same predetermined range, but the numerical values of the non-DNA features may be normalized to be within the same order of magnitude as the DNA features. For a non-DNA feature that may be described by a scale (e.g., a feature that is a continuous variable), a feature may be modeled as a distribution with a maximum and minimum range. The range of the feature may be normalized to a predetermined range. For example, for a feature that is modeled as a Gaussian distribution, any values that are beyond a certain number of standard deviations (e.g., 3) may be capped as the maximum or minimum range. Other values within the range may be normalized to the predetermined range (e.g., between 0 and 1). For features that may be discrete, such as those features that are identified into different categories (e.g., binary categories of the presence or absence of a trait, multi-class categories such as eye colors, SNP values), the categories may be assigned to various number values, such as integers. The features that are expressed as numerical representations may also be normalized so that DNA features and non-DNA features may be combined more efficiently as input features of a machine learning model.

The feature vector is inputted into a machine learning model that generates 320 a prediction of whether the target individual has the trait. In some embodiments, the machine learning model is a supervised machine learning model. In other embodiments, the machine learning model is an unsupervised machine learning model. A prediction may be generated 320 as a probability of the target individual having the trait. The prediction may also be generated 320 as a classification, classifying the individual as having the trait, not having the trait, or having a variant of the trait. For example, an individual may be classified as having brown eyes, blue eyes, green eyes, or hazel eyes. In some embodiments, data representing the prediction is transmitted to a user interface for display.

The prediction may account for the heritability of the trait, referred to as an inheritance probability. The inheritance probability may be based on the likelihood that the target individual inherited the trait from one or more members of the target individual's family tree who have the trait. The inheritance probability may also be based on the likelihood that the target individual passed on the trait to one or more members of the target individual's family tree. The inheritance probability may be used as one of the features in the input feature vector for the machine learning model. The inheritance probability may also be used as a post-processing factor after the machine learning model has generated a prediction. The prediction may also account for the prevalence of the trait among one or more genetic communities of the target individual. In some embodiments, this is accounted for as a feature in the feature vector. In other embodiments, the initial prediction is updated based on a community prediction, which is the likelihood the individual has the trait based on the prevalence of the trait within the genetic community of the individual. For example, an initial prediction may estimate that there is 65% likelihood that an individual is a carrier of a trait based on an inheritance prediction. However, based on a higher or lower community prediction of the trait, the initial prediction may be updated accordingly.

Figure 4:
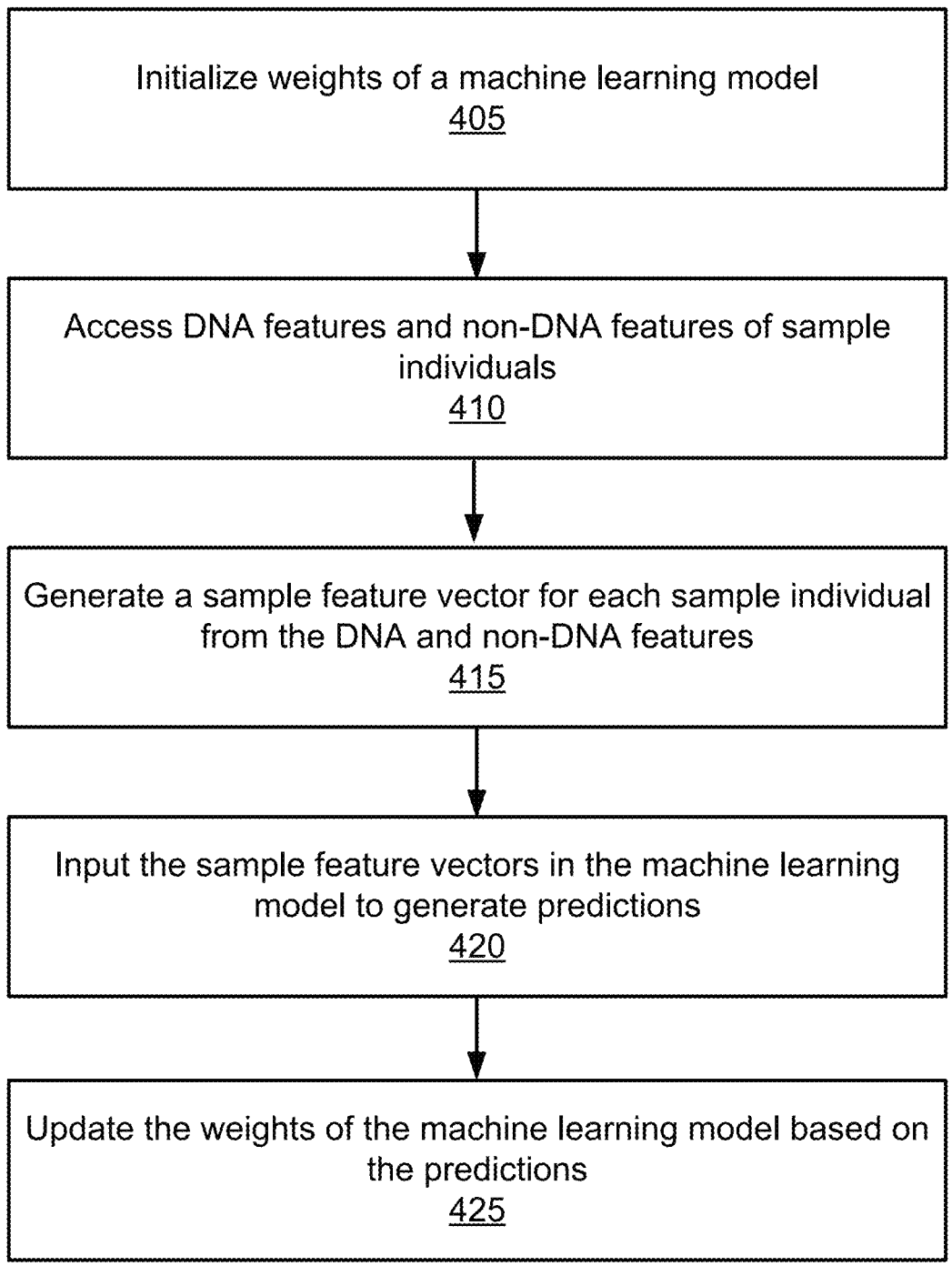
FIG. 4 illustrates a method of training a machine learning model to predict a trait of a target individual, in accordance with an embodiment.

FIG. 4 illustrates a method 400 of training a machine learning model to predict a trait of a target individual, in accordance with an embodiment. Weights of a machine learning model are initialized 405 with a set of initial values. DNA features of sample individuals are accessed 410. Sample individuals, which may also be referred to as training samples, may be individuals that affirmatively have the trait or affirmatively do not have the trait, and are labeled accordingly. Sample individuals may be identified based on information stored in the genealogy data store 200, genetic data store 205, and/or individual profile store 210. Non-DNA features of the sample individuals are also accessed 410.

In some embodiments, the non-DNA features of the sample individuals are normalized. Non-DNA features may be normalized record-wise and/or content-wise. Record-wise normalization may account for the variations in the ways records are formatted, the type of information stored in a record, the amount of information that is stored in a record, and how data in a record is referenced. For example, a record may store an individual's name in a "Last Name, First Name, Middle Initial" format, while another record may store the same individual's name in a "First Name, Middle Name, Last Name" format. Content-wise normalization accounts for the variations in data values in different records. Content-wise normalization may include consolidating spelling-variants of record data (e.g., consolidating colloquial and/or period-specific job titles) and filtering data based on prevalence among sample individuals (e.g., filtering out job titles that are associated with fewer than a threshold number of sample individuals).

A sample feature vector is generated 415 for each sample individual based on a subset of the corresponding DNA and non-DNA features of the sample individual. Sample feature vectors may include numerical values for the DNA and non-DNA features based on numerical encodings of the DNA and non-DNA features, discussed in detail with reference to FIG. 3. A DNA feature may be selected if it is disproportionately associated with individuals in different genetic communities. For example, DNA features of various SNP sites that correspond to known differences in the phenotypes of individuals belonging to different genetic communities may be selected. Non-DNA features may be similarly selected. Alternatively, or additionally, non-DNA features may be selected based on the subset of DNA features. The number of features that are added to a sample feature vector may be reduced using selection algorithms or by using the most significant DNA-features in an association study such as a genome-wide association study (GWAS). The non-DNA feature scale may be adjusted to be on par with the DNA features. This may be done by reducing the number of non-DNA features based on the number of selected DNA features and/or by adjusting the numerical values of the non-DNA features so that they are within the same order of magnitude as the DNA features. Details of example association studies are further discussed in U.S. patent application Ser. No. 16/598,988, filed on Oct. 10, 2019, entitled "Phenotype Trait Prediction with Threshold Polygenic Risk Score."

The sample feature vectors of the sample individuals are inputted 420 into the machine learning model to generate a prediction of whether each sample individual has the trait. Predictions may be calculated as a probability of the sample individual having the trait, or as a classification indicating whether the individual has the trait or a particular variant of a trait. The weights of the machine learning model are updated 425 based on the prediction and the label associated with each sample individual. The weights may be iteratively updated until the model converges. In some embodiments, the weights are updated until a difference between the label and the prediction of the sample individuals is within a threshold difference. Alternatively, or additionally, the weights may be updated until a percentile of accurate predictions is within a threshold percentile across the training data. The performance of the model may be stratified by genetic community, ethnicity population, and the like.

In various embodiments, a wide variety of machine learning techniques may be used. Examples of which include different forms of unsupervised learning, clustering, supervised learning such as random forest classifiers, support vector machines (SVM) such as kernel SVMs, gradient boosting, linear regression, logistic regression, and other forms of regressions. Deep learning techniques such as neural networks, including recurrent neural networks (RNN) and long short-term memory networks (LSTM), may also be used.

In a certain embodiment, a machine learning model may include certain layers, nodes, and/or coefficients. The machine learning model may be associated with an objective function, which generates a metric value that describes the objective goal of the training process. For example, the training may intend to reduce the error rate of the model by reducing the output value of the objective function, which may be called a loss function. Other forms of objective functions may also be used, particularly for unsupervised learning models whose error rates are not easily determined due to the lack of labels.

In one embodiment, a supervised learning technique is used. The sample individuals may be classified into two groups, which may be referred to as a positive training set (individuals with the trait) and a negative training set (individuals without the trait). In some supervised learning techniques, the objective function of the machine learning algorithm may be the training error rate in predicting the trait in the two training sets. For example, the objective function may be cross-entropy loss. In another embodiment, an unsupervised learning technique is used and the sample individuals used in training are not labeled as having or not having a trait. Various unsupervised learning techniques such as clustering may be used. In yet another embodiment, the machine learning model may be semi-supervised.

Taking an example of a neural network as the machine learning model, training of a neural network may include forward propagation and backpropagation. A neural network may include an input layer, an output layer, and one or more intermediate layers that may be referred to as hidden layers. Each layer may include one or more nodes, which may be fully or partially connected to other nodes in adjacent layers. In forward propagation, the neural network performs computation in the forward direction based on outputs of a preceding layer. The operation of a node may be defined by one or more functions. The functions that define the operation of a node may include various computation operations such as convolution of data with one or more kernels, recurrent loop in RNN, various gates in LSTM, etc. The functions may also include an activation function that adjusts the weight of the output of the node. Nodes in different layers may be associated with different functions.

Each of the functions in a machine learning model may be associated with different coefficients that are adjustable during training. In addition, some of the nodes in a neural network each may also be associated with an activation function that decides the weight of the output of the node in forward propagation. Common activation functions may include step functions, linear functions, sigmoid functions, hyperbolic tangent functions (tan h), and rectified linear unit functions (ReLU). The data of a sample individual in the training set may be converted to a feature vector in a manner described above. After a feature vector is inputted into the neural network and passes through a neural network in the forward propagation, the results may be compared to the training label of the sample individual to determine the neural network's performance. The process of prediction may be repeated for other sample individuals in the training sets to compute the value of the objective function in a particular training round. In turn, the neural network performs backpropagation by using coordinate descent such as stochastic coordinate descent (SGD) to adjust the coefficients in various functions to improve the value of the objective function.

Multiple rounds of forward propagation and backpropagation may be performed. Training may be completed when the objective function has become sufficiently stable (e.g., the machine learning model has converged) or after a predetermined number of rounds for a particular set of training samples. A trained model may be used to predict the trait of a new subject.

While the training is described using a neural network as an example, a similar training process may be used for other suitable machine learning algorithms. In training a machine learning algorithm, various regularization techniques and cross-validation techniques may be used to reduce the chance of over-fitting the algorithm.

In some embodiments, a different machine learning model is maintained for different traits, environmental conditions, and genetic communities. Additional models may be generated as new traits are identified or inquired about. In some embodiments, machine learning models are updated when new sample individuals are identified. For example, the machine learning model may be updated when new individuals respond to surveys, or when new users create accounts with the computing server 130. Additionally, the machine learning model may be updated with a predetermined frequency, e.g., every month, six months, year, etc.

Figure 5:
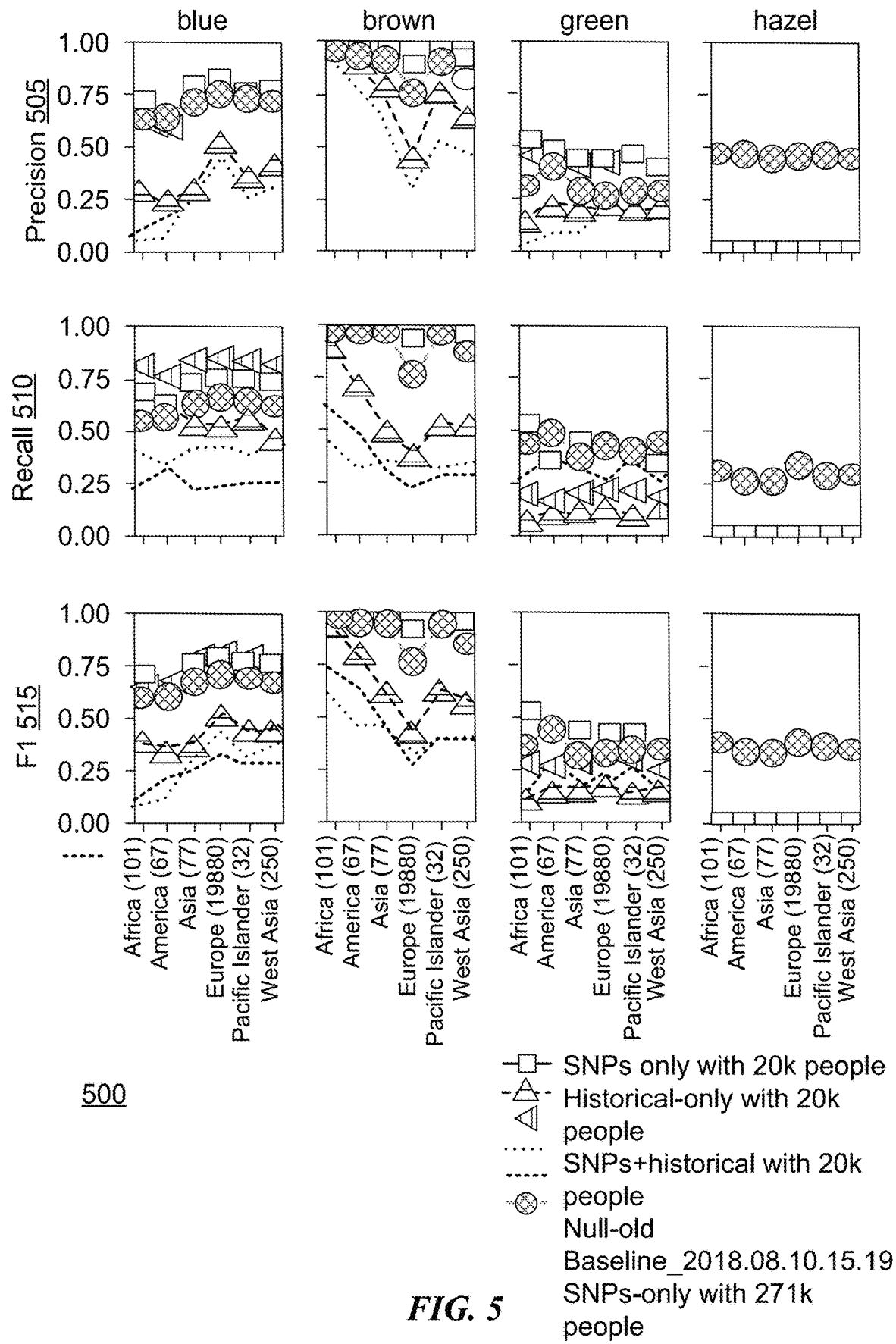
FIG. 5 illustrates sample results of machine learning models to predict traits of individuals.

FIG. 5 illustrates example results 500 of machine learning models to predict traits of individuals. In particular, FIG. 5 illustrates example results 500 that use machine learning to predict eye color phenotype using SNP data and historical data. The training set used to train the machine learning model includes 20,000 people with known eye colors, SNP features, and historical features. The example results 500 show the precision 505, recall 510, and F1 515 of eye color predictions across different genetic communities. The example results 500 show that the machine learning model's recall for blue eyes increased when historical features and SNP features were accounted for. In the absence of SNP features, the historical features can predict eye color better than a null model. The example results 500 may be aggregated across different genetic communities to identify which traits are prominent in different continental ethnicities (as shown) and/or in different genetic communities. Example results 500 can also be used to identify which traits are easier to accurately predict in different genetic communities.

Example Tree-Based Trait Prediction Models

Figure 6:
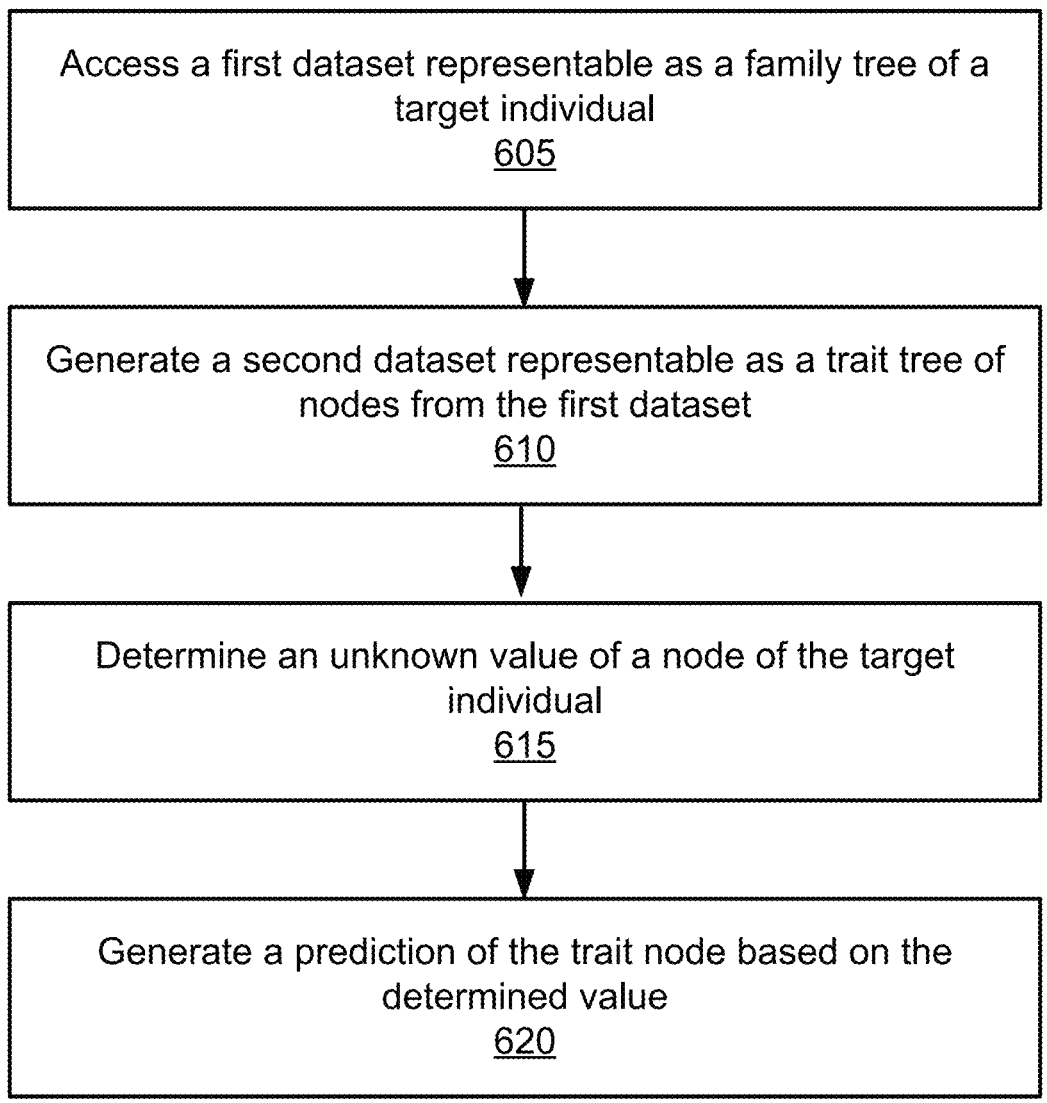
FIG. 6 illustrates a method of predicting a trait of a target individual using an example tree-based approach, in accordance with an embodiment.

FIG. 6 illustrates a method 600 of predicting a trait of a target individual using an example tree-based approach, in accordance with an embodiment. Examples of traits include genetic traits and environmental conditions. To predict the trait of the target individual, a first dataset presentable as a family tree of the target individual is accessed 605. For example, the dataset may store data of the family tree and may be visually represented as a family tree. The family tree may describe relationships among the target individual and relatives of the individual. The family tree may include a full or partial pedigree structure, birth years, gender, marital relations, and genetic relations among individuals in the family tree. The first dataset may also include the historical and medical records of the individuals in the family tree. The historical and medical records may include information about a trait exhibited by individuals in the family tree, such as a genetic trait (e.g., appearance traits, anthropometric traits, metabolic traits, health status traits, other behavioral traits), environmental condition (e.g., diet, exercise patterns, urban or rural lifestyles, residence types), or socioeconomic status (e.g., family income, education level of target individual, education level of parents and/or grandparents).

A second dataset is generated 610 from the first dataset that is representable as a trait tree. For example, data may be stored in a tabular format, key-value pair format, pointer, array, etc. and the data visually may be represented as a tree based on the data and the format of the data. The trait tree may comprise nodes for the target individual and one or more related individuals (e.g., one or more members of the target individual's family tree). In some embodiments, the values of the nodes are binary, indicating whether or not an individual has a trait or a particular variant of a trait. For example, nodes representing individuals that have a trait may have a value of 1, nodes representing individuals that do not have the trait may have a value of 0, and nodes representing individuals for which it is unknown if they have trait may not have a value. For example, it is not known if the target individual has the trait, so a first node representing the target individual has an unknown value. In these embodiments, separate trait trees may be maintained for different variants of a trait. For example, a trait tree for brown hair may be separately maintained from a trait tree for red hair. In other embodiments, a trait tree may include node values that represent multiple variants of a trait. In these embodiments, the values of the node are coded based on the number of known variants of the trait. For example, a trait tree may be generated for eye color, and an individual with brown eyes may be represented as a node with a value of 1, an individual with green eyes may be represented as a node with a value of 2, and an individual with blue eyes may be represented as a node with a value of 3. As with the binary trait tree, when it is not known whether an individual has a trait, the corresponding node may not have a value or may be represented with an alternative value (such as a character or symbol).

The unknown value of the node of the target individual is determined 615 at least based on an inheritance probability propagated from a known value of a second node along one or more branches of the trait tree connecting the node of the target individual to the second node. For example, if the second node corresponds to the mother of the target individual, the inheritance probability is propagated from the node of the mother to the node of the target individual and represents the likelihood the target individual inherited the trait. In some embodiments, the unknown value is determined based on a probabilistic model or function, such as a likelihood function or log-likelihood function. The unknown value may be determined by maximizing or minimizing the function. A prediction of the trait of the target individual is generated 620 based on the determined value of the first node. For example, it may be determined that the target individual has a trait or a variant of the trait if the determined value is greater than or equal to a threshold value. Alternatively, it may be determined that the target individual has the trait or the variant of the trait if the determined value is less than a threshold value.

In some embodiments, the unknown value of the target individual is further based on a community probability. A community probability reflects the prevalence of the trait among individuals associated with a genetic community of the target individual. The community probability may be estimated based on how many individuals in the community exhibit the trait. Further, the community probability may be normalized based on how many individuals associated with other genetic communities also exhibit the trait. In some embodiments, a community probability is added to the feature vector of the target individual. In other embodiments, the prediction of the trait of the target individual is updated based on the community probability. For example, the value on the first node representing the target individual may be recalculated based on the inheritance probability and the community probability. In some embodiments, this recalculation may be performed as a conditional statement that reflects the probability the target individual has the trait given the inheritance probability in view of the community probability. Alternatively, the recalculation may be performed as a conditional statement that reflects the probability the target individual has the trait given the community probability in view of the inheritance probability.

There may be additional individuals in the trait tree represented by nodes with unknown values. In some embodiments, the unknown value of an additional node may be determined at least based on the inheritance probability propagated from the known value of the second node along one or more branches connecting the second node and the additional node. The unknown value of the additional node may also be based on the prediction of the trait of the target individual. For example, it may be determined whether a sister of the target individual with an unknown node value has the trait based on the inheritance probability propagated from the node of the mother to the node of the sister and the prediction of the target individual.

Further, the unknown value of the target individual and the unknown values of the additional individuals may be determined by propagating calculations of node values in backwards and forwards directions along at least one branch of the trait tree. The value of each of the one or more nodes can be recalculated until a consistent conclusion is reached. Node values may be recalculated by updating or maximizing a likelihood or log-likelihood function. For example, the values of the one or more nodes may be recalculated until a net change in the values of the one or more nodes is within a threshold net change (e.g., the trait tree converges). In some embodiments, these calculations also account for the population probabilities of the additional individuals represented by the one or more nodes.

Figure 7:
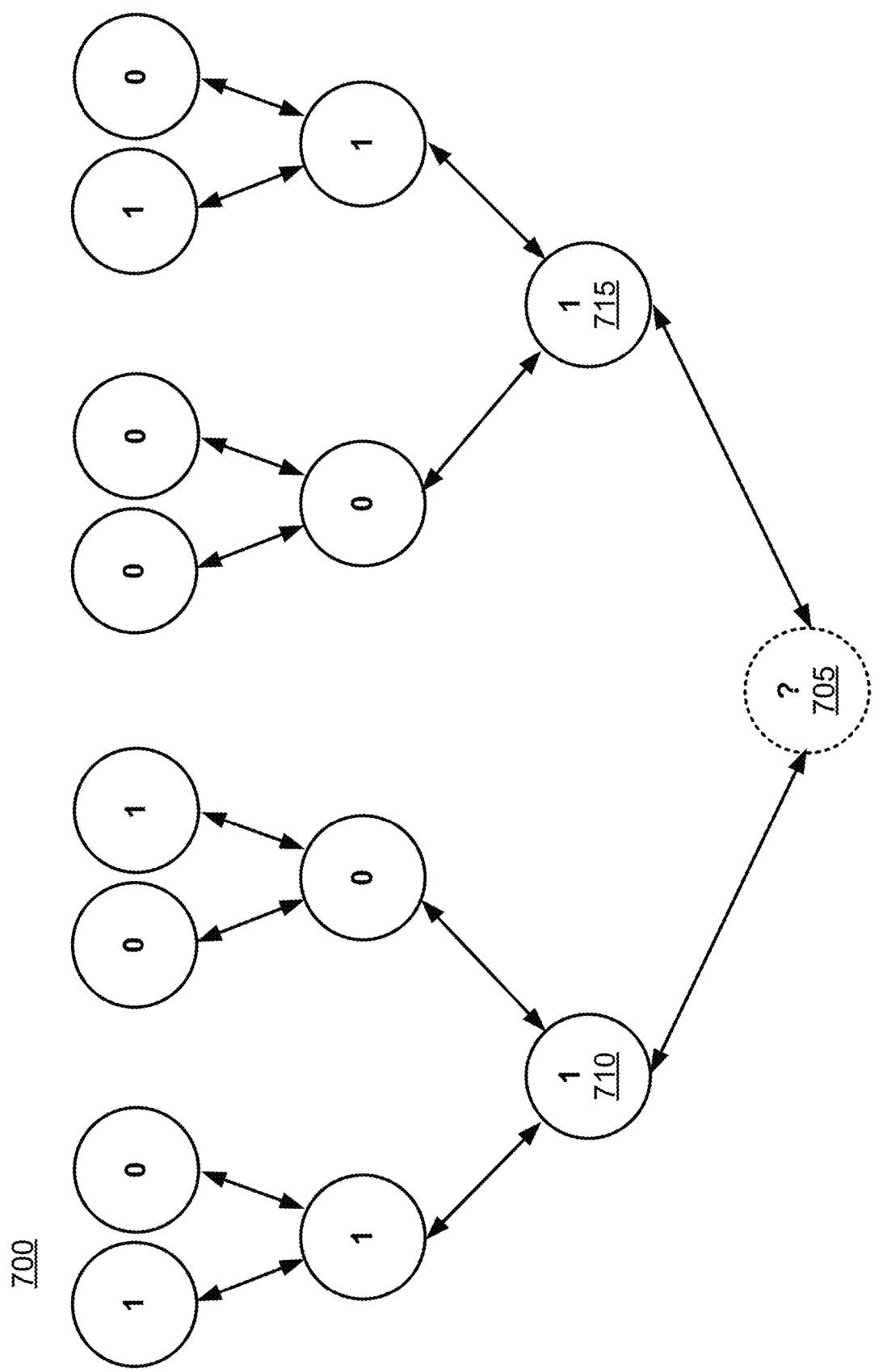
FIG. 7 illustrates an example trait tree, in accordance with an embodiment.

FIG. 7 illustrates an example trait tree 700, in accordance with an embodiment. The trait tree 700 illustrates how heritability estimates can be extended to a probabilistic model to predict the likelihood a target individual 705 has a trait. As discussed with reference to FIG. 6, a trait tree is generated based on data representable as a family tree of a target individual. Individuals in the trait tree 700 are represented as nodes with values indicating the presence or absence of a trait (or variant of a trait) in an individual. The trait tree also provides an indication when it is not known whether an individual has the trait. As shown, the node representing the target individual 705 has an unknown value, and both of the nodes representing the parents of the target individual 705 have known values.

Based on the data in the trait tree, the computing server 130 can predict whether the target individual 705 is likely to have the trait. The prediction may be determined by calculating an inheritance probability between the target individual 705 and one or more relatives represented in the trait tree 700. The inheritance probability is propagated along at least one branch of the trait tree that connects the node of the target individual 705 and the one or more relatives with known node values. In the trait tree 700 shown, the node values of the target individual's 705 parents are known and are each represented with a 1, indicating that parents have the trait represented in the trait tree. The likelihood the target individual 705 has the trait may be based on an inheritance probability propagated from a first parent 710 to the target individual 705, an inheritance probability propagated from a second parent 715 to the target individual 705, or an inheritance probability propagated from both the first parent 710 and second parent 715 to the target individual 705. In some embodiments, the likelihood the target individual 705 has the trait may additionally be based on a community probability of a genetic community of the target individual 705. When the target individual 705 is a member of more than one genetic community, a community probability corresponding to each of the genetic communities of the target individual may be considered.

For example, the probability an individual has a trait may be calculated according to Equation 1, which calculates the probability an individual has the trait given the presence of the trait in a parent of the individual.

$$P(\text{trait}_{individual}=1)=P(\text{trait}=1|\text{trait}_{parent}=1) \quad (1)$$

In Equation 1, $P(\text{trait}_{individual}=1)$ represents the probability an individual has the trait given a parent of the individual has the trait, represented by the term $\text{trait}_{parent}=1$.

Alternatively, the probability an individual has a trait may be calculated according to Equation 2, which accounts for the prevalence of the trait in a community of the individual and the presence and/or absence of the trait in a parent of the individual.

$$P(\text{trait}_{individual}=1) = \frac{P(\text{trait}_{parent}=1)*P(\text{trait}_{parent}=1|\text{trait}=1)}{P(\text{trait}_{community}=1)} + \quad (2)$$
$$P(\text{trait}=1|\text{trait}_{parent}=0)$$

In Equation 2, $P(\text{trait}_{community}=1)$ represents the community probability. Alternatively, the probability an individual has the trait may be calculated according to Equation 3, which may be used to calculate the probability an individual has the trait.

$$P(trait_{individual} = 1) = \frac{P(trait_{parent} = 0) * P(trait_{parent} = 0 \mid trait = 1)}{P(trait_{community} = 1)} \quad (3)$$

Figure 8:
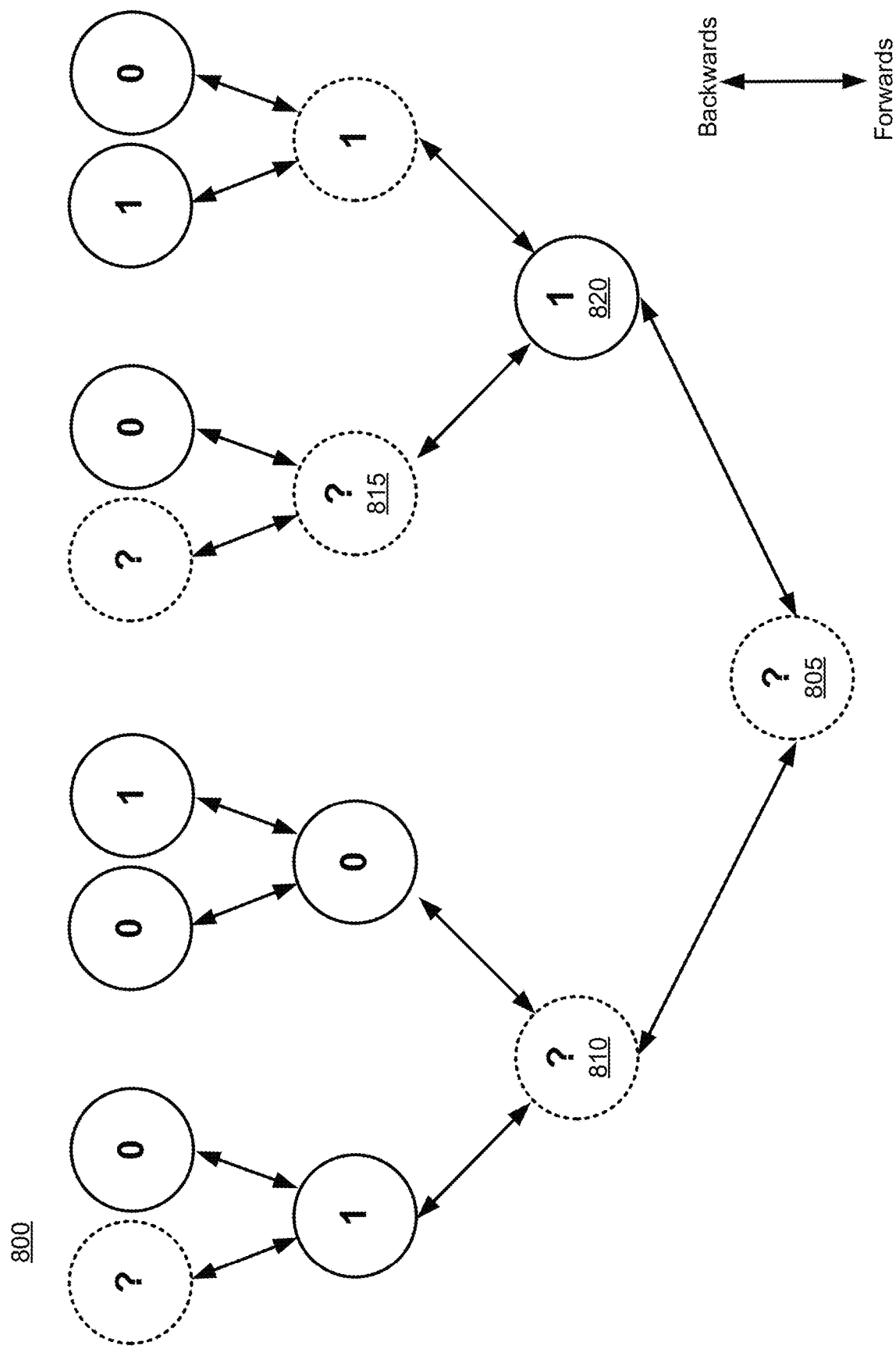
FIG. 8 illustrates an extension of heritability estimates over a trait tree, in accordance with an embodiment.

FIG. 8 illustrates an extension of heritability estimates over a trait tree 800, in accordance with an embodiment. The trait tree 800 includes multiple nodes with unknown values, namely the nodes representing individual 805, individual 810, and individual 815. The computing server 130 can estimate the values of the nodes by computing directional probabilities up and down branches of the trait tree 800 until a predictive convergence within the trait tree 800 is reached. Initial predictions for each of the nodes may be determined by generating feature vectors of the individuals represented by nodes with unknown values, as discussed in detail with reference to FIG. 3. The feature vectors of individuals represented by nodes with unknown values are inputted into a trained machine learning to predict whether the individuals have the trait.

The predictions of the trait may be updated by iteratively passing through the trait tree 800 in forwards and backwards directions along one or more branches of the trait tree and updating the probabilities accordingly. For example, in a forward direction, the value of node 810 may be determined by the inheritance probability given that a first parent has the trait 0 and the second parent has the trait 1. A community probability may also be applied to further adjust the value. The determined value of node 810 may be a value between 0 and 1. Given the determined value of node 810 and the value 1 in the node 820, the predicted value of the target individual as represented by the node 805 may be determined using inheritance probability and, in some embodiments, also the community probability. In a backward direction, using a function such as a likelihood or log-likelihood function, the predicted values at node 810, 815, etc. may be updated. For example, the predicted value at node 810 may be based on the current predicted value of the target individual 805 by updating or maximizing a likelihood or log-likelihood function. The determining of values using the function may further propagate to the end nodes of various branches in the trait tree 800. In a next round of iteration, predictions values of various nodes with unknown traits are updated again in the forward direction first then in the backward direction. The probabilities may be continuously updated until a consist conclusion is reached (e.g., the trait tree 800 converges). A predictive convergence may be reached when a net change in node value predictions is less than a threshold change.

Example Determination Process of Enriched Record Collections

FIG. 9 illustrates a method 900 of predicting a set of enriched record collections for a genetic community, in accordance with an embodiment. Enriched record collections may be used to identify and/or characterize different genetic communities. Record data in the set of enriched record collections may be compared against pedigree data for individual family trees or pre-stitched family trees to update either data in the set of enriched record collections or in the pedigree data. Enriched record collections may also be provided to users researching the histories of different genetic communities as a tool to narrow and/or identify relevant data sources.

To identify a set of enriched record collections of a genetic community, individuals belonging to the genetic community are identified 905. Individuals belonging to a genetic community may be individuals who are genetically associated, individuals that are linked by one or more family trees, individuals that are a part of a carrier population, individuals that are a part of an admixed population, individuals that have self-selected as being a part of a genetic community, or a combination thereof.

Candidate record collections associated with the individuals of the genetic community are accessed 910. Candidate record collections may include records of the individuals belonging to the genetic community and/or records of relatives of the individuals belonging to the genetic community. Candidate record collections may include DNA, DNA-derived, and non-DNA data that are associated with members of the genetic community. Examples of record collections may include collections from birth certificate databases, death certificate databases, marriage certificate databases, adoption databases, draft registration databases, veterans databases, military databases, property records databases, census databases, voter registration databases, phone databases, address databases, newspaper databases, immigration databases, family history records databases, local history records databases, business registration databases, motor vehicle databases, and the like.

A community count is determined 915 for each candidate record collection in the set of candidate record collections. A community count may be determined 915 based on one or more of: how often the candidate record collection is associated with a family tree of the individuals of the genetic community, how often a member of the genetic community is mentioned in a candidate record collection, how often a genetic community at large is mentioned in a candidate record collection, how often members of a genetic community access a candidate record collection, and the like.

A background count of each candidate record collection in the set is also determined 920. A background count may be determined 920 based on how often the candidate record collection is associated with the family trees across a plurality of genetic communities identified by the computing server 130. A background count for a candidate record collection may also be based one or more of: how often members of other genetic communities are mentioned in the candidate record collection, how many other genetic communities are associated with the candidate record collection, how frequently members of other genetic communities access the candidate record collection, and the like.

A set of enriched record collections is identified 925 based on a comparison of the community count and background count of each candidate record collection. The comparison may be performed using statistical enrichment tests (e.g., Fisher's Exact Test, Chi-square Test). In some embodiments, the statistical enrichment tests are used to compare the community counts and background counts of a candidate record collection for different communities. For example, a community count and background count of a candidate record collection determined for an Irish community may be compared to the community count and background count for the same candidate record collection determined for a German community. An indication that a set of enriched record collections is related to the genetic community may be provided for display on a user interface 115.

Various enrichment techniques may be used. In one embodiment, the enrichment analysis may include Fisher's exact test to identify one or more candidate record collections that is strongly associated with a genetic community.

In another embodiment, chi-square tests may be used to perform the enrichment analysis. Other suitable enrichment analysis may include the calculation of log odds ratios, measures of parametric and non-parametric correlations, such as Pearson's r, or Spearman's rho, to look at other kinds of enrichments or relationships. In an enrichment analysis, an enrichment score may be determined for the association between a candidate record collection and a genetic community. The enrichment score may represent a strength of association between the target trait and the genetic community. For example, the enrichment score may correspond to a p-value of the relevancy of the candidate record collection in a genetic community. In one embodiment, the enrichment score may take the form of the odds ratio of an individual in a record collection belonging to a particular genetic community. The computing server 130 may compare the odds ratios among various record collections. Record collections with the odds ratios that exceed a certain threshold and that are within the top certain percentile may be determined as the record collections being enriched. Conversely, record collections with the odds ratios that are below another threshold or at certain bottom percentile may be determined as record collections that have reduced likelihoods of being associated with a genetic community. Other suitable statistical methods may be used to conduct the enrichment analysis.

The set of enriched record collections of a genetic community may be analyzed to understand the regional, social, and economic history of the genetic community. Similarities and differences among different genetic communities may be identified by comparing the enriched record collections of respective genetic communities. An analysis of enriched record collections may also be used to identify and/or characterize previously uncharacterized or unknown genetic communities. For example, a genetic community of Central American Catholics may be identified based on a set of enriched record collections that includes Baptisms performed in Mexico between 1560-1950, a record collection of Baptisms performed in Guatemala performed between 1730 and 1917, and a record collection of Catholic Church records in Chiapas, Mexico between 1558 and 1978. A genetic community of German Lutherans may be characterized based on a set of enriched record collections that includes Lutheran baptisms, marriages, and burials performed in Wurttemberg, Germany between 1500 and 1985, Lutheran baptisms, marriages, and burials performed in Baden, Germany between 1402 and 1985, and Lutheran baptisms, marriages, and burials performed in Bavaria, Germany between 1556 and 1973. The histories of the Central American Catholic community and the German Lutheran community may then be compared using the sets of enriched record collections to understand the environmental and historical factors that shaped each community.

Content may be created for a genetic community based on its respective set of enriched record collections. Content may be created using natural language processing methods on structured data. Collections may contain records with structured data such as birth, death, census, and draft data. This data may be turned into structured/tabled data using methods such as optical character recognition. Structured/tabled data can be input into templates to generate characterizations of community attributes during different periods of time. For example, the template may inform a user of the number of births, deaths, and marriages per year on average in a community during a period of time. Content may also be created using natural language processing methods on unstructured data. Unstructured data may include data that cannot be aggregated into a common format. For example, newspapers, yearbooks, and journals may be classified as unstructured data. Data extracted from these sources may provide information about the politics, sporting and cultural events, and finances of the time. This information can be aggregated to provide users insights into the opinions and interests of community members during different eras. For example, the information may provide insight into the musical preferences and political opinions of a subset of community members that were alive in America during the 1950's.

Example Determination Process of Enriched Characteristics of a Community

FIG. 10 illustrates a method 1000 of identifying an enriched characteristic of a genetic community, in accordance with an embodiment. An enriched characteristic is a characteristic, such as a trait, phenotype, historical environmental condition, location, occupation, family arrangement, or socioeconomic status, that is more prevalent in one genetic community than in other genetic communities. Characteristics may also be referred to as traits, which may be any phenotypes, preferences, environmental factors, events associated with individuals, or any other suitable identifiable things of the individuals. For example, an example trait may be whether an individual has or does not have a certain appearance trait (e.g., hair curl, eye color). Another example trait may be the birth location of the individual. U.S. patent application Ser. No. 15/203,776, entitled "Genetic and Genealogical Analysis for Identification of Birth Location and Surname Information," filed on Jul. 6, 2016, describes possible embodiments of enriched birth location and surname identification and assignment. Yet another example trait may be the native language spoken by the individual. Other suitable traits could include, but are not limited to, personality traits (e.g. morning person versus night person), wellness traits (e.g. male-pattern baldness), lifestyle traits (e.g., exercise habits), preference traits (lifestyle preferences such as party-going preference, other preferences such as music and dancing preference), beliefs, opinions, cultural traits, behavioral traits, traits collected from historical records, traits collected from electronic health or electronic medical records, vitamin traits, sensitivity traits (e.g. aversion to cilantro), and sensory traits (e.g. ability to sense an asparagus metabolite).

Enriched characteristics may be identified by comparing the prevalence of a characteristic in a first genetic community with the prevalence of the characteristic among a second genetic community, a set of additional genetic communities, and/or all genetic communities identified by the computing server 130. For example, the prevalence of red hair among a Swedish community may be compared to the prevalence of red hair among an Austrian community, all communities located within Europe, etc.

Enriched characteristics may also be identified for subsets of a genetic community. A subset of a genetic community may include a set of genetic community members that all exhibit a particular attribute. Examples of attributes may include belonging to a historical era, gender, age, pedigree position, and the like. For example, an enriched occupation may be identified among women in a genetic community that were between the ages of 25 and 40 years old between the years 1920-1950. Enriched characteristics among a subset may be identified by comparing the prevalence of a characteristic among members of the subset and the prevalence of the characteristic among the entire genetic community. Alternatively, enriched characteristics of a subset may be identified by comparing the prevalence of a characteristic among different subsets of the same genetic community. For example, occupations among Chinese men and women in the 19$^{th}$ century may be compared. Further, enriched characteristics of the subset may be identified by comparing the prevalence of a characteristic among the subset with the prevalence of the characteristic among other genetic communities and/or subsets of other genetic communities. For example, eye color among German newborns in the 18$^{th}$ century may be compared to eye color among Nigerian newborns in the 18$^{th}$ century.

Additionally or alternatively, underenriched characteristics may be identified. Underenriched characteristics may be a set of characteristics members of a genetic community are unlikely to have. For example, it may be determined that blue eye color is unlikely to be exhibited by members of a Middle Eastern community, and curly is unlikely to be exhibited by members of an Asian community.

The computing server 130 may identify characteristics of a genetic community based on the data of members of the genetic community. For example, characteristics may be identified from DNA and non-DNA data, as discussed in detail with reference to FIG. 3. The non-DNA data may be normalized into a common format so that content can be aggregated across records. In some embodiments, characteristics are identified from a set of enriched record collections associated with the genetic community. For example, an enriched characteristic may be identified among Caribbean Islanders based on data in an enriched set of record collections that includes Marriages in the Dominican Republic 1743-1929, Baptisms in the Dominican Republic, and Births and Baptisms in the Caribbean 1590-1928.

To identify an enriched characteristic of a genetic community, a community frequency is determined 1005 for one or more of the identified characteristics. A community frequency is based on one or more of: how often a respective characteristic is exhibited in individuals belonging to the genetic community, how often a characteristic is associated with a family tree of an individual, how often a characteristic is mentioned in records of an individual or genetic community, and the like.

A background frequency for each of the one or more characteristics is determined 1010 based on how often a respective characteristic is exhibited in individuals of any of the plurality of genetic communities identified by the computing server 130. For example, a background frequency may be based on how often a characteristic is associated with all or most users of the computing server 130, mentioned in data of the genealogy data store 200, genetic data store 205, individual profile store 210, or maintained in the record collections and libraries of the computing server 130.

One or more enriched characteristics exhibited by individuals belonging to the genetic community are identified 1015 based on a comparison of the community frequency and the background frequency of each of the one or more characteristics. Comparisons may be based on a difference, ratio, or any other suitable comparison method. A characteristic may be identified as an enriched characteristic if a difference between the community frequency and the background frequency of the respective characteristic is greater than a threshold difference. Alternatively, or additionally, a characteristic may be identified as an enriched characteristic if the ratio between the community frequency and the background frequency of the respective characteristic is greater than a threshold ratio. A characteristic may be identified as an underenriched characteristic if a difference between the community frequency and background frequency is less than a threshold different. A characteristic may also be identified as an underenriched characteristic if a ratio between the community frequency and the background frequency of a trait is less than a threshold ratio.

An aggregate spatial-temporal description of a genetic community may be generated by identifying enriched characteristics for subsets of individuals belonging to the genetic community. An aggregate spatial-temporal description gives insight into changes in phenotypes and/or historical environments of a genetic community over time and/or over different geographic regions. To generate an aggregate spatial-temporal description of a genetic community, the data of the genetic community is filtered to create subsets of the genetic community. Data may be filtered based on an attribute of the community members, such as gender, age, historical period, or pedigree position (e.g., great-grandparents). The aggregate spatial-temporal description of the characteristic will change based on which attribute is chosen. For example, if the data is filtered based on time period, the aggregate spatial-temporal description will provide insight into the changes in enriched characteristics over time, and if the data is filtered based on gender, the aggregate spatial-temporal description will provide insight into the changes in enriched characteristics among men and women.

Enriched characteristics for each of the subsets are identified by 1) determining a community frequency for subset for one or more characteristics, and 2) determining a background frequency for each of the one or more characteristics, and 3) comparing the community frequency with the background frequency. In some embodiments, the background frequency is based on the frequency of the characteristic among members of the genetic community at large. For example, to identify an enriched characteristic among Italian women born between the years 1960 and 1990, the background frequency of a characteristic may be based on the prevalence of the characteristic among the Italian genetic community at large. In alternative embodiments, the background frequency of a characteristic is based on the prevalence of the characteristic among all genetic communities identified by the computing server 130, or is based on the prevalence of the characteristic among one or more different subsets of the genetic community. A spatial-temporal aggregate description is generated by repeating this process for the additional subsets of the genetic community and comparing the results to visualize which characteristics were enriched among the different subsets of the genetic community. Statistical enrichment tests may be performed to determine which genetic communities and/or subsets of genetic communities are more likely to have a particular phenotype or historical environment. Genetic communities can be compared by comparing their respective aggregate spatial-temporal descriptions. Statistical enrichment tests may be performed to determine which genetic communities are more likely to have a particular characteristic. For example, a comparison may be performed to determine which phenotypes or genetic histories are unique to a genetic community.

Figure 11:
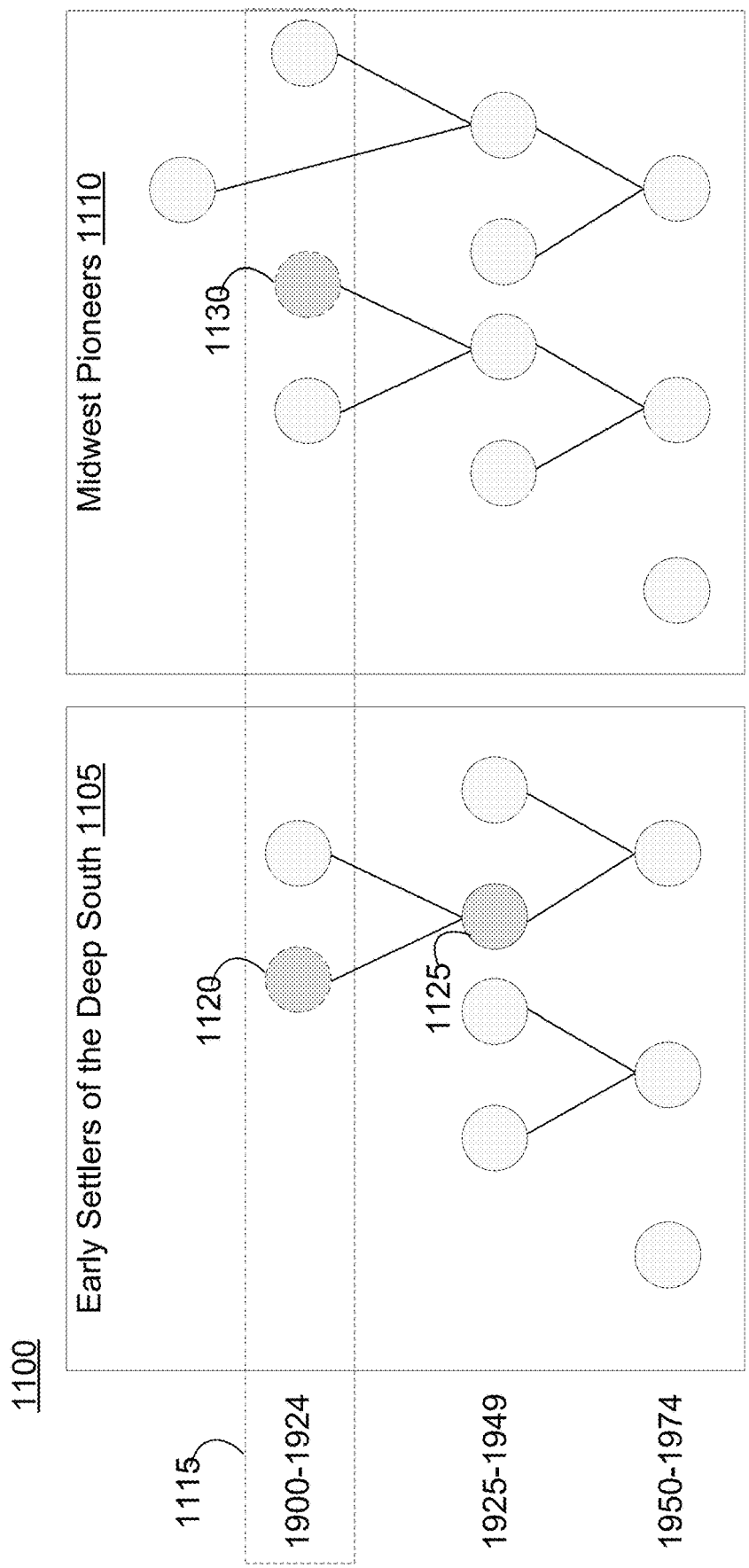
FIG. 11 is an example illustration of family trees in different genetic communities, in accordance with an embodiment.

FIG. 11 is an example illustration 1100 of family trees in different genetic communities, in accordance with an embodiment. The illustration 1100 shows what happens when information about the genetic community of an individual is aggregated based on the pedigree structure of the individual. Records and photos are attached to the family trees of individuals and may be analyzed generation-wise by analyzing the records and photos of community members alive during a particular period, and/or branch-wise by analyzing the records associated with individuals along a branch of the pedigree structure.

The illustration 1100 shows two genetic communities, namely Early Settlers of the Deep South 1105 and Midwest Pioneers 1110. Individual circles within each genetic community represent individuals associated with a particular generation and a particular family tree. For example, individuals represented by circle 1120 are members of the genetic community Early Settlers of the Deep South 1105, were born between 1900-1924, are the ancestors of individuals represented by circle 1125, who were born between 1925-1950. Darkened circles represent ancestors associated with historical records. To compare the enriched characteristics of different genetic communities within a particular time period, the records of community members in each of the different genetic communities alive during the time period are analyzed and compared. For example, to compare the enriched characteristics of Early Settlers of the Deep South 1105 and the enriched characteristics of Midwest Pioneers 1110 alive during the first quarter of the 20$^{th}$ century 1115, the records of the individuals represented by circle 1120 and circle 1130 are analyzed and compared. To compare the enriched characteristics of individuals in the same genetic community alive during different time periods, the available records of community members in each time period are compared. For example, to compare the enriched characteristics of Early Settlers of the Deep South 1105 alive during the second quarter of the 20$^{th}$ century and the enriched characteristics of Early Settlers of the Deep South 1105 alive during the third quarter of the 20$^{th}$ century, the records of the individuals represented by circle 1125 and circle 1120 are analyzed and compared.

Figure 12:
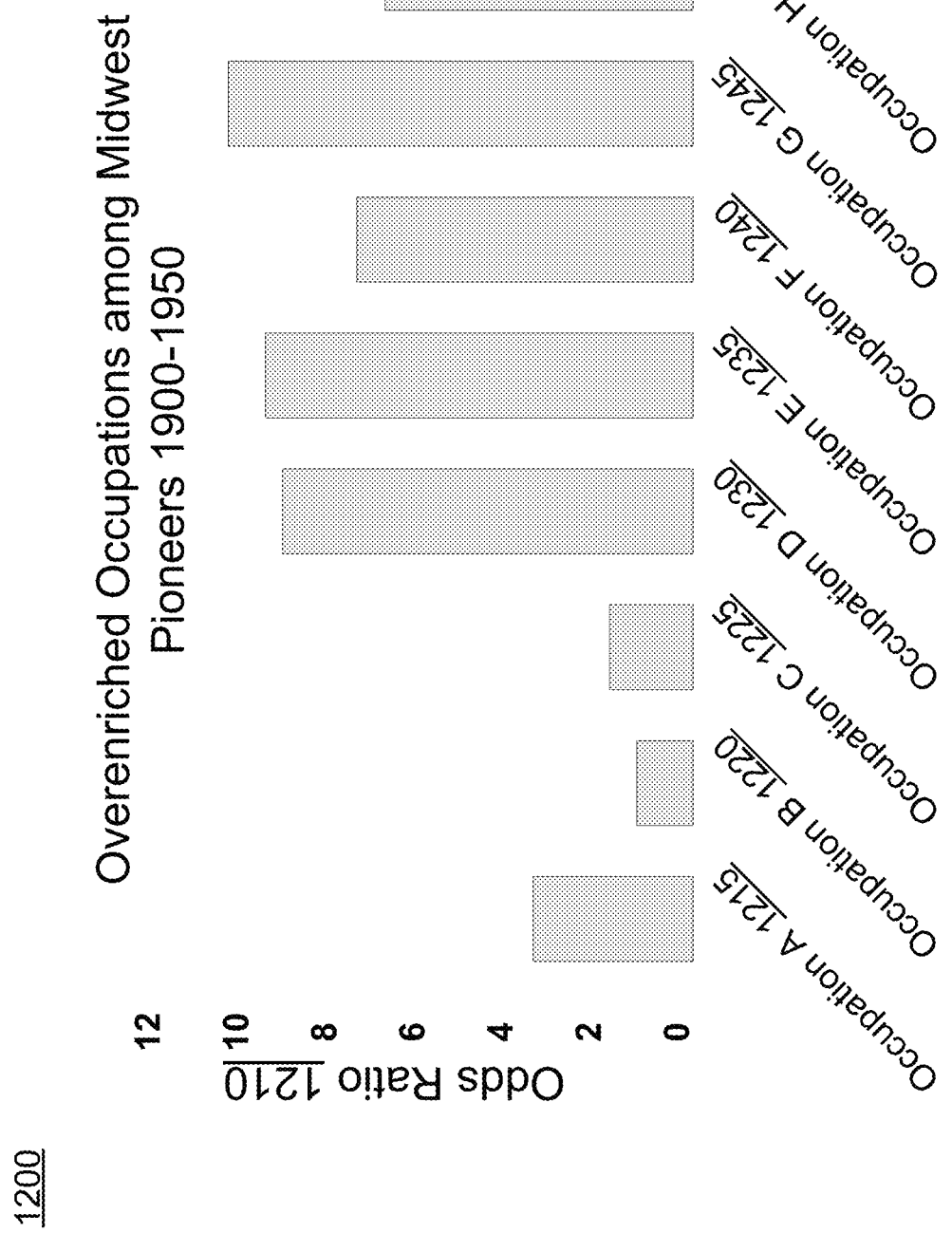
FIG. 12 illustrates the results of an enrichment analysis performed on characteristics of a genetic community, in accordance with an embodiment.

FIG. 12 illustrates the results 1200 of an enrichment analysis performed on characteristics of a genetic community, in accordance with an embodiment. The results of an enrichment analysis may be expressed as an odds ratio. An odds ratio is defined as the odds that, given a community, an individual who is a member of the community has the characteristic over the odds that the individual does not have the characteristic. An odds ratio may provide better insight into which characteristics are enriched in a community than frequency, because frequency may provide more insight into a time period than into a particular community.

As shown, the enrichment analysis was performed on the occupations of individuals belonging to the community Midwest Pioneers who worked between the years 1900 and 1950. The results of the analysis identify a set of occupations that are overenriched in the community of Midwest Pioneers. The value of each occupation is expressed as an odds ratio 1210. In some embodiments, an occupation is overenriched if the corresponding odds ratio is above a threshold odds ratio. In some embodiments, an occupation is overenriched if the occupation is within a threshold percentile of all occupations associated with a community (e.g., occupations within the 90$^{th}$ percentile). An occupation may also be overenriched if the occupation is more common in the genetic community than in other genetic communities maintained by the computing server 130. As shown, occupation A 1215, occupation B 1220, occupation C 1225, occupation D 1230, occupation E 1235, occupation F 1240, occupation G 1245, and occupation H 1250 are all overenriched occupations among Midwest pioneers between 1900 and 1950. These occupations are unique to the community and may inform a story of both the era and the community.

Figure 13:
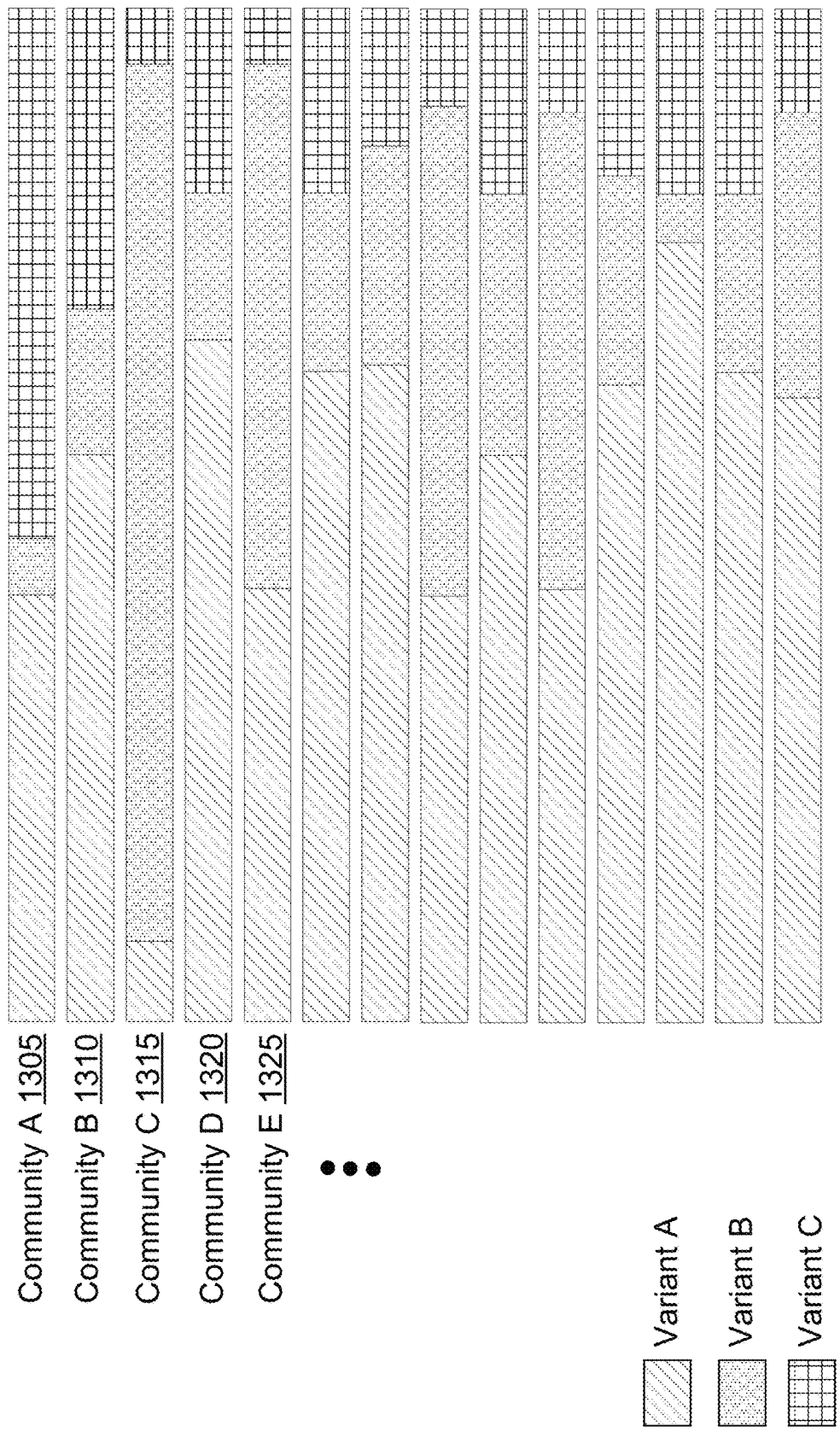
FIG. 13 illustrates a distribution of trait variants among different genetic communities, according to one embodiment.

FIG. 13 illustrates a distribution 1300 of trait variants among different genetic communities, according to one embodiment. As discussed with reference to FIG. 10, enriched characteristics may be identified for different genetic communities. When a characteristic, such as eye color, as more than one variant, the distribution of the variants among different communities may be compared to visualize which variants are enriched in different communities. The illustration shown is based on a characteristic with three variants, namely, Variant A, Variant B, and Variant C. The distribution of the three variants among different communities provides insight into the prevalence of different traits among community members. For example, in community A 1305, Variant C is the most prevalent variant of the characteristic, followed by Variant A, then Variant B. In community B 1310 and community D 1320, Variant A is the most prevalent, and in community C 1315 and community E 1325, Variant B is the most prevalent. Similarities among different communities may be identified based on the distribution 1300. For example, it may be inferred that when two communities have similar distributions, they may share ancestors more recently than when two communities have dissimilar distributions.

Computing Machine Architecture

Figure 14:
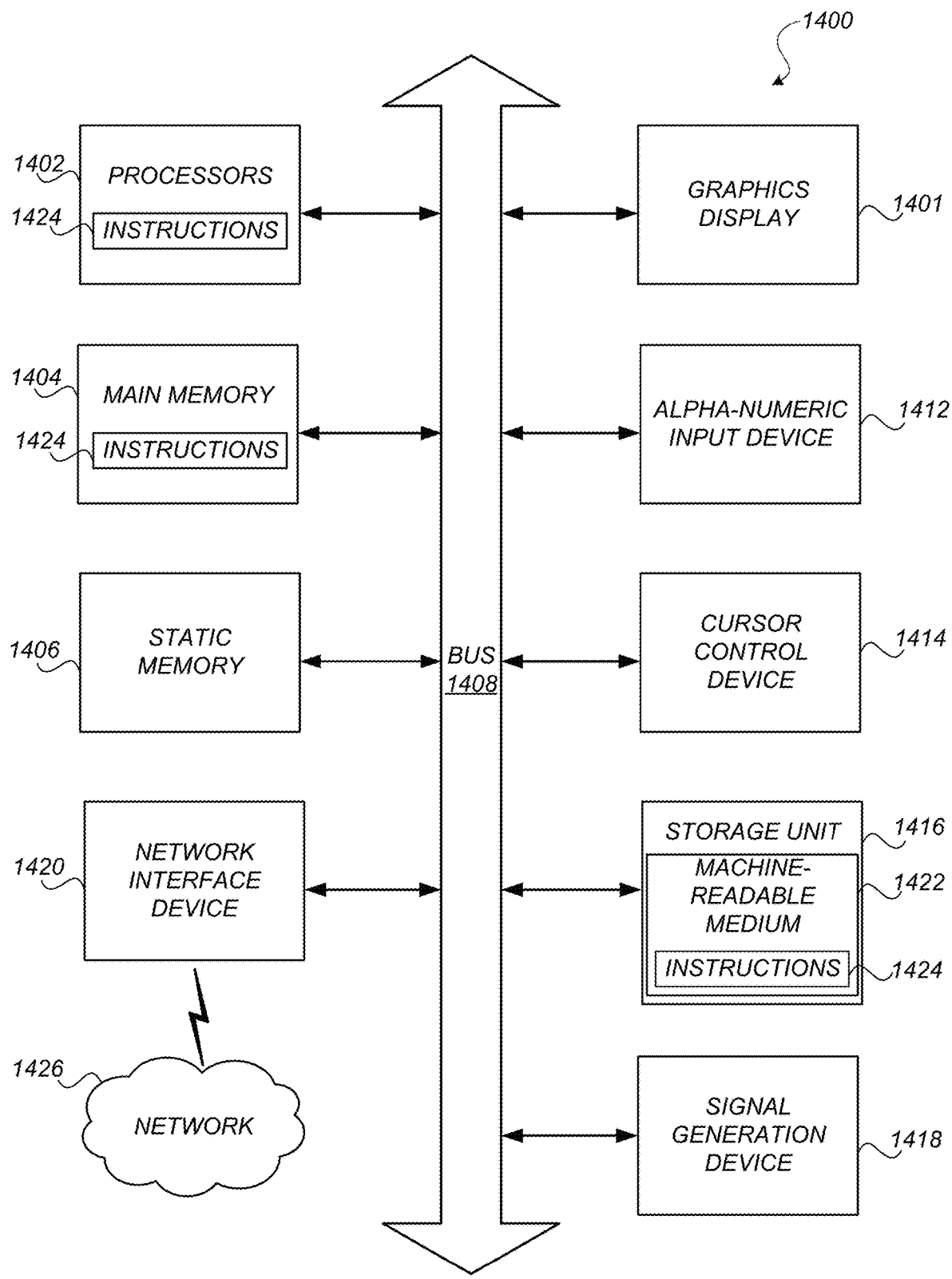
FIG. 14 is a block diagram of an example computing device, in accordance with an embodiment.

FIG. 14 is a block diagram illustrating components of an example computing machine that is capable of reading instructions from a computer-readable medium and execute them in a processor (or controller). A computer described herein may include a single computing machine shown in FIG. 14, a virtual machine, a distributed computing system that includes multiples nodes of computing machines shown in FIG. 14, or any other suitable arrangement of computing devices.

By way of example, FIG. 14 shows a diagrammatic representation of a computing machine in the example form of a computer system 1400 within which instructions 1424 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 14 may correspond to any software, hardware, or combined components shown in FIGS. 1 and 2, including but not limited to, the client device 110, the computing server 130, and various engines, interfaces, terminals, and machines shown in FIG. 2. While FIG. 14 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1424 that specify actions to be taken by that machine. Further, while only a single machine is illustrated, the term "machine" and "computer" may also be taken to include any collection of machines that individually or jointly execute instructions 1424 to perform any one or more of the methodologies discussed herein.

The example computer system 1400 includes one or more processors 1402 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1400 may also include a memory 1404 that store computer code including instructions 1424 that may cause the processors 1402 to perform certain actions when the instructions are executed, directly or indirectly by the processors 1402. Instructions can be any directions, commands, or orders that may be stored in different forms, such as equipment-readable instructions, programming instructions including source code, and other communication signals and orders. Instructions may be used in a general sense and are not limited to machine-readable codes.

One and more methods described herein improve the operation speed of the processors 1402 and reduces the space required for the memory 1404. For example, the machine learning methods described herein reduces the complexity of the computation of the processors 1402 by applying one or more novel techniques that simplify the steps in training, reaching convergence, and generating results of the processors 1402. The algorithms described herein also reduces the size of the models and datasets to reduce the storage space requirement for memory 1404.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1400 may include a main memory 1404, and a static memory 1406, which are configured to communicate with each other via a bus 1408. The computer system 1400 may further include a graphics display unit 1410 (e.g., a plasma display panel (PDP), a liquid crystal display (LCD), a projector, or a cathode ray tube (CRT)). The graphics display unit 1401, controlled by the processors 1402, displays a graphical user interface (GUI) to display one or more results and data generated by the processes described herein. The computer system 1400 may also include alphanumeric input device 1412 (e.g., a keyboard), a cursor control device 1414 (e.g., a mouse, a trackball, a joystick, a motion sensor, or other pointing instrument), a storage unit 1416 (a hard drive, a solid-state drive, a hybrid drive, a memory disk, etc.), a signal generation device 1418 (e.g., a speaker), and a network interface device 1420, which also are configured to communicate via the bus 1408.

The storage unit 1416 includes a computer-readable medium 1422 on which is stored instructions 1424 embodying any one or more of the methodologies or functions described herein. The instructions 1424 may also reside, completely or at least partially, within the main memory 1404 or within the processor 1402 (e.g., within a processor's cache memory) during execution thereof by the computer system 1400, the main memory 1404 and the processor 1402 also constituting computer-readable media. The instructions 1424 may be transmitted or received over a network 1426 via the network interface device 1420.

While computer-readable medium 1422 is shown in an example embodiment to be a single medium, the term "computer-readable medium" should be taken to include a single medium or multiple media (e.g., a centralized or distributed database, or associated caches and servers) able to store instructions (e.g., instructions 1424). The computer-readable medium may include any medium that is capable of storing instructions (e.g., instructions 1424) for execution by the processors (e.g., processors 1402) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. patent application Ser. No. 15/591,099, entitled "Haplotype Phasing Models," filed on Oct. 19, 2015, (2) U.S. patent application Ser. No. 15/168,011, entitled "Discovering Population Structure from Patterns of Identity-By-Descent," filed on May 28, 2016, (3) U.S. "Reducing Error in Predicted Genetic Relationships," filed on Apr. 13, 2017, (4) U.S. patent application Ser. No. 15/209,458, entitled "Local Genetic Ethnicity Determination System," filed on Jul. 13, 2016, (5) U.S. patent application Ser. No. 14/029,765, entitled "Identifying Ancestral Relationships Using a Continuous stream of Input," filed on Sep. 17, 2013, (6) U.S. patent application Ser. No. 16/598,988, entitled "Phenotype Trait Prediction with Threshold Polygenic Risk Score," filed on Oct. 10, 2019, and (7) U.S. patent application Ser. No. 15/203,776, entitled "Genetic and Genealogical Analysis for Identification of Birth Location and Surname Information," filed on Jul. 6, 2016.

What is claimed is:

1. A computer-implemented method for improving a machine learning model used for trait detection using genetic data, the computer-implemented method comprising:
   collecting a set of DNA features of sample individuals;
   collecting a set of non-DNA features of the sample individuals;
   applying one or more transformations to the set of non-DNA features to generate numerical values representing the non-DNA features;
   creating a training set comprising feature vectors that combine the set of DNA features and the set of non-DNA features;
   training the machine learning model using the training set;
   accessing a target set of DNA features of a target individual;
   accessing a target set of non-DNA features of the target individual;
   generating a target feature vector that combines the target set of DNA features and the target set of non-DNA features, the target feature vector including a target set of numerical values, at least a first one of the numerical values representing one of the DNA features, at least a second one of the numerical values representing one of the non-DNA features; and
   inputting the target feature vector to the machine learning model to generate a prediction of whether the target individual has a trait.

2. The computer-implemented method of claim 1, wherein training the machine learning model using the training set comprises:
   initializing weights of the machine learning model with an initial set of values;
   accessing the set of DNA features of the sample individuals, each of the sample individuals associated with a label indicating whether the sample individual is known to have the trait;
   accessing the set of non-DNA features of the sample individuals;
   inputting the feature vectors to the machine learning model to generate a prediction of whether each sample individual has the trait; and
   updating the weights of the machine learning model based on the prediction and the label associated with each of the sample individuals.

3. The computer-implemented method of claim 2, further comprising:
   identifying a subset of DNA features of the sample individual that are disproportionately associated with individuals in different genetic communities; and
   identifying a subset of non-DNA features based on the subset of DNA features.

4. The computer-implemented method of claim 1, wherein the set of non-DNA features include one or more of the following: historical records, medical records, survey responses, or digital photographs.

5. The computer-implemented method of claim 1, wherein the target set of non-DNA features of the target individual include non-DNA features of related individuals that are genetically related to the target individual.

6. The computer-implemented method of claim 1, further comprising:
   normalizing the target set of DNA features and/or the target set of non-DNA features of the target individual.

7. The computer-implemented method of claim 6, wherein normalizing comprises bringing one of the numerical values of a non-DNA feature to a range that is in the same order of magnitude of a numerical value of one of the DNA features.

8. The computer-implemented method of claim 1, wherein at least one of the DNA features in the target set is a value of single nucleotide polymorphism (SNP) at a genetic locus of the target individual.

9. The computer-implemented method of claim 1, wherein the target individual is a member of a genetic community, and wherein the prediction of whether the target individual has the trait is an initial prediction, the method further comprising:
   determining a community prediction based on a prevalence of the trait among the genetic community; and updating the initial prediction of whether the target individual has the trait based on the community prediction.

10. A computer-implemented method of predicting a trait of a target individual, comprising:

accessing a first dataset representing a family tree of the target individual, the family tree describing relationships among the target individual and related individuals who are related to the target individual;

collecting a set of historical records of the related individuals, the set of historical records comprising at least a first type of features and a second type of features;

applying one or more transformations to the first type of features and the second type of features to generate feature vectors including numerical values that represent the historical records;

inputting the feature vectors into a machine learning model to determine one or more traits of one or more related individuals;

generating, from the first dataset and the one or more traits determined by the machine learning model, a second dataset representing a trait tree, the trait tree comprising nodes representing the target individual and one or more related individuals, each node being connected to at least another node in accordance with the relationships described in the family tree, the nodes comprising (i) a first node representing the target individual, the first node having an unknown value, and (ii) a second node having a known value representing one of the traits of one of the related individuals represented by the second node, the one of traits determined by the machine learning model;

determining the unknown value of the first node, the unknown value determined at least based on an inheritance probability propagated from the known value of the second node along one or more branches of the trait tree, determining the unknown value comprising:

iteratively, by a processor, passing through the trait tree in forwards and backwards directions, and updating, by the processor, the inheritance probability until the unknown value and the inheritance probability converge; and generating a prediction of the trait of the target individual based on a determined value of the first node.

11. The computer-implemented method of claim 10, further comprising:

identifying a third node in the trait tree representing another related individual, the third node having an unknown value; and determining the unknown value of the third node, the unknown value determined at least based on the inheritance probability propagated from the known value of the second node along one or more branches of the trait tree and the prediction of the trait of the target individual.

12. The computer-implemented method of claim 10, wherein generating the prediction further comprises:

estimating a community trait probability based on a prevalence of the trait among individuals associated with a genetic community of the target individual; and updating the prediction of the trait based on the community trait probability.

13. The computer-implemented method of claim 10, wherein the unknown value of the first node is determined based on a probabilistic model.

14. The computer-implemented method of claim 10, wherein the unknown value of the first node is determined based on updating the unknown values of one or more nodes by propagating calculations of inheritance probabilities in backwards and forwards directions along at least one branch of the trait tree.

15. A computer-implemented method of predicting a set of enriched record collections for a genetic community among a plurality of genetic communities, comprising:

identifying individuals belonging to the genetic community;

accessing a set of candidate record collections;

determining a community count of each candidate record collection in the set based on how often the candidate record collection is associated with one of the individuals;

determining a background count of each candidate record collection in the set based on how often the candidate record collection is associated with any individual in the plurality of genetic communities; and identifying the set of enriched record collections of the genetic community based on a comparison of the community count and background count of each candidate record collection, the set of enriched record collections comprises a first set of records of structured data and a second set of records of unstructured data;

applying one or more transformations to the first set of records of structured data and the second set of records of unstructured data to generate feature vectors including numerical values that represent values in the structured data and the unstructured data;

inputting the feature vectors into a natural-language processing machine learning model to identify one or more characterizations of the genetic community.

16. The computer-implemented method of claim 15, further comprising:

providing an indication that the set of enriched record collections is related to the genetic community.

17. The computer-implemented method of claim 15, wherein the genetic community includes individuals that are genetically matched.

18. The computer-implemented method of claim 15, wherein the genetic community includes individuals that are linked by one or more family trees.

19. The computer-implemented method of claim 15, wherein the genetic community includes individuals that are a part of a carrier population.

20. The computer-implemented method of claim 15, wherein the genetic community includes individuals that are a part of an admixed population.

21. The computer-implemented method of claim 15, wherein the one or more characterizations is an enriched characteristic among the individuals belonging to the genetic community.

22. The computer-implemented method of claim 21, wherein identifying the enriched characteristic comprises:

determining a community frequency for the one or more characteristics, a respective community frequency based on how often a respective characteristic is associated with individuals belonging to the genetic community;

determining a background frequency for each of the one or more characteristics, a respective background frequency based on how often the respective characteristic exhibits in individuals of any of the plurality of genetic communities;

identifying one or more enriched characteristics among the individuals belonging to the genetic community based on a comparison of the community frequency and background frequency of each of the one or more characteristics.

23. The computer-implemented method of claim 22, wherein at least one of the enriched characteristics includes a trait, a phenotype, a historical environment, a location, an occupation, family arrangement, or socioeconomic status.

24. The computer-implemented method of claim 15, further comprising:
   filtering the set of enriched record collections based on an attribute of the individuals belonging to the genetic community, wherein the attribute includes one or more of: a gender, an age, a historical era, or a pedigree.

25. The computer-implemented method of claim 15, wherein the set of enriched record collections includes DNA data of the individuals belonging to the genetic community.

26. The computer-implemented method of claim 15, further comprising:
   generating content items for the genetic community based on the set of enriched record collections.

* * * * *